US009566456B2

(12) United States Patent
Sverdlik et al.

(10) Patent No.: US 9,566,456 B2
(45) Date of Patent: Feb. 14, 2017

(54) ULTRASOUND TRANSCEIVER AND COOLING THEREOF

(75) Inventors: Ariel Sverdlik, Tel-Aviv (IL); Or Shabtay, Kibbutz Farod (IL)

(73) Assignee: CardioSonic Ltd., Tel-Aviv (IL)

( * ) Notice: Subject to any disclaimer, the term of this patent is extended or adjusted under 35 U.S.C. 154(b) by 0 days.

(21) Appl. No.: 13/879,400

(22) PCT Filed: Oct. 18, 2011

(86) PCT No.: PCT/IB2011/054641
§ 371 (c)(1),
(2), (4) Date: Apr. 14, 2013

(87) PCT Pub. No.: WO2012/052927
PCT Pub. Date: Apr. 26, 2012

(65) Prior Publication Data
US 2013/0204167 A1 Aug. 8, 2013

Related U.S. Application Data

(63) Continuation-in-part of application No. 13/049,022, filed on Mar. 16, 2011.
(Continued)

(51) Int. Cl.
*A61N 7/02* (2006.01)
*A61B 17/22* (2006.01)
(Continued)

(52) U.S. Cl.
CPC ........... *A61N 7/022* (2013.01); *A61B 17/2202* (2013.01); *A61B 2017/00106* (2013.01);
(Continued)

(58) Field of Classification Search
CPC ................ A61N 7/02; A61N 7/022; A61B 2018/00994; A61B 17/2202
(Continued)

(56) References Cited

U.S. PATENT DOCUMENTS 5,226,847 A 7/1993 Thomas, III et al.
5,421,338 A 6/1995 Crowley et al.
(Continued)

FOREIGN PATENT DOCUMENTS

CN 1279595 1/2001
CN 101610735 12/2009
(Continued)

OTHER PUBLICATIONS

Invitation to Pay Additional Fees Dated Aug. 5, 2013 From the International Searching Authority Re. Application No. PCT/IL2013/050341.
(Continued)

*Primary Examiner* — Jocelyn D Ram

(57) ABSTRACT

An ultrasonic transceiver device for producing ultrasonic beams comprises a body vibratable at ultrasonic frequencies and an extensive surface for beam emanation, the device configured to produce an unfocused, or alternatively a focused, power beam for thermal tissue damage, the power beam being produced by vibration over the body of the transceiver and emanating from the extent of the surface, whereby the extensive surface becomes subject to convective cooling when immersed in a fluid by a chimney effect set up by said unfocused beam.

34 Claims, 19 Drawing Sheets
(9 of 19 Drawing Sheet(s) Filed in Color)

Related U.S. Application Data

(60) Provisional application No. 61/393,947, filed on Oct. 18, 2010, provisional application No. 61/393,947, filed on Oct. 18, 2010.

(51) Int. Cl.
  *A61B 17/00* (2006.01)
  *A61N 7/00* (2006.01)

(52) U.S. Cl.
  CPC .............. *A61B 2017/22008* (2013.01); *A61B 2017/22051* (2013.01); *A61B 2017/22081* (2013.01); *A61B 2090/378* (2016.02); *A61N 2007/003* (2013.01); *A61N 2007/0039* (2013.01); *A61N 2007/0052* (2013.01); *A61N 2007/0078* (2013.01)

(58) Field of Classification Search
  USPC ........ 606/27, 41, 33, 20–26, 45, 49, 169, 28
  See application file for complete search history.

(56) References Cited

U.S. PATENT DOCUMENTS

| | | | |
|---|---|---|---|
| 5,471,988 A | 12/1995 | Fujio et al. | |
| 5,524,630 A | 6/1996 | Crowley | |
| 5,590,653 A * | 1/1997 | Aida et al. | 600/411 |
| 5,620,417 A | 4/1997 | Jang et al. | |
| 5,657,760 A | 8/1997 | Ying et al. | |
| 5,699,804 A | 12/1997 | Rattner | |
| 5,707,367 A | 1/1998 | Nilsson | |
| 5,735,280 A | 4/1998 | Sherman et al. | |
| 5,762,066 A | 6/1998 | Law et al. | |
| 5,895,355 A * | 4/1999 | Schaer | 600/381 |
| 5,895,356 A | 4/1999 | Andrus et al. | |
| 5,971,949 A * | 10/1999 | Levin et al. | 604/22 |
| 6,042,556 A * | 3/2000 | Beach et al. | 601/3 |
| 6,073,048 A | 6/2000 | Kieval et al. | |
| 6,077,225 A | 6/2000 | Brock-Fisher | |
| 6,117,101 A | 9/2000 | Diederich et al. | |
| 6,119,041 A * | 9/2000 | Pomeranz et al. | 607/101 |
| 6,165,127 A | 12/2000 | Crowley | |
| 6,210,393 B1 * | 4/2001 | Brisken | 604/508 |
| 6,216,041 B1 * | 4/2001 | Tierney et al. | 607/101 |
| 6,235,024 B1 * | 5/2001 | Tu | 606/41 |
| 6,261,233 B1 | 7/2001 | Kantorovich | |
| 6,296,619 B1 | 10/2001 | Brisken et al. | |
| 6,379,320 B1 | 4/2002 | Lafon et al. | |
| 6,428,477 B1 | 8/2002 | Mason | |
| 6,451,013 B1 * | 9/2002 | Bays et al. | 606/27 |
| 6,500,121 B1 | 12/2002 | Slayton et al. | |
| 6,511,428 B1 * | 1/2003 | Azuma et al. | 600/439 |
| 6,511,436 B1 | 1/2003 | Asmar | |
| 6,527,759 B1 | 3/2003 | Tachibana et al. | |
| 6,547,788 B1 * | 4/2003 | Maguire et al. | 606/41 |
| 6,599,288 B2 | 7/2003 | Maguire et al. | |
| 6,607,502 B1 | 8/2003 | Maguire et al. | |
| 6,645,147 B1 | 11/2003 | Jackson et al. | |
| 6,740,040 B1 | 5/2004 | Mandrusov et al. | |
| 6,752,805 B2 | 6/2004 | Maguire et al. | |
| 6,953,460 B2 * | 10/2005 | Maguire et al. | 606/27 |
| 6,955,173 B2 * | 10/2005 | Lesh | 128/898 |
| 6,978,174 B2 | 12/2005 | Gelfand et al. | |
| 7,001,336 B2 * | 2/2006 | Mandrusov et al. | 600/439 |
| 7,037,271 B2 | 5/2006 | Crowley | |
| 7,084,004 B2 * | 8/2006 | Vaiyapuri et al. | 438/106 |
| 7,156,816 B2 * | 1/2007 | Schwartz et al. | 601/2 |
| 7,162,303 B2 | 1/2007 | Levin et al. | |
| 7,166,098 B1 | 1/2007 | Steward et al. | |
| 7,220,233 B2 * | 5/2007 | Nita et al. | 601/2 |
| 7,220,258 B2 * | 5/2007 | Myhr | 606/28 |
| 7,220,261 B2 | 5/2007 | Truckai et al. | |
| 7,285,116 B2 * | 10/2007 | de la Rama et al. | 606/27 |
| 7,326,201 B2 * | 2/2008 | Fjield et al. | 606/27 |
| 7,341,583 B2 * | 3/2008 | Shiono et al. | 606/13 |
| 7,344,529 B2 * | 3/2008 | Torchia et al. | 606/13 |
| 7,347,859 B2 * | 3/2008 | Garabedian et al. | 606/41 |
| 7,410,486 B2 | 8/2008 | Fuimaono et al. | |
| 7,460,369 B1 * | 12/2008 | Blish, II | 361/699 |
| 7,470,241 B2 * | 12/2008 | Weng et al. | 601/3 |
| 7,479,106 B2 * | 1/2009 | Banik et al. | 600/159 |
| 7,510,536 B2 | 3/2009 | Foley et al. | |
| 7,538,425 B2 * | 5/2009 | Myers et al. | 257/714 |
| RE40,815 E | 6/2009 | Kudaravalli et al. | |
| 7,540,846 B2 * | 6/2009 | Harhen et al. | 601/2 |
| 7,540,870 B2 * | 6/2009 | Babaev | 606/20 |
| 7,563,260 B2 * | 7/2009 | Whitmore et al. | 606/21 |
| 7,617,005 B2 | 11/2009 | Demarais et al. | |
| 7,620,451 B2 | 11/2009 | Demarais et al. | |
| 7,621,929 B2 | 11/2009 | Nita et al. | |
| 7,647,115 B2 | 1/2010 | Levin et al. | |
| 7,653,438 B2 | 1/2010 | Deem et al. | |
| 7,655,005 B2 | 2/2010 | Bhola | |
| 7,678,104 B2 | 3/2010 | Keidar | |
| 7,704,212 B2 * | 4/2010 | Wekell et al. | 600/488 |
| 7,713,210 B2 * | 5/2010 | Byrd et al. | 600/459 |
| 7,717,948 B2 | 5/2010 | Demarais et al. | |
| 7,727,228 B2 * | 6/2010 | Abboud et al. | 606/21 |
| 7,736,317 B2 | 6/2010 | Stephens et al. | |
| 7,756,583 B2 | 7/2010 | Demarais et al. | |
| 7,762,954 B2 * | 7/2010 | Nix et al. | 600/459 |
| 7,771,372 B2 | 8/2010 | Wilson | |
| 7,819,868 B2 * | 10/2010 | Cao et al. | 606/41 |
| 7,824,348 B2 | 11/2010 | Barthe et al. | |
| 7,850,683 B2 | 12/2010 | Elkins et al. | |
| 7,850,685 B2 * | 12/2010 | Kunis et al. | 606/41 |
| 7,853,333 B2 | 12/2010 | Demarais | |
| 7,854,733 B2 * | 12/2010 | Govari | 606/27 |
| 7,883,506 B2 * | 2/2011 | McIntyre et al. | 606/27 |
| 7,940,969 B2 | 5/2011 | Nair et al. | |
| 8,216,216 B2 * | 7/2012 | Warnking et al. | 606/27 |
| 8,221,402 B2 * | 7/2012 | Francischelli et al. | 606/27 |
| 8,401,667 B2 * | 3/2013 | Gustus et al. | 607/99 |
| 8,419,729 B2 * | 4/2013 | Ibrahim et al. | 606/41 |
| 8,540,662 B2 * | 9/2013 | Stehr et al. | 604/41 |
| 8,568,403 B2 * | 10/2013 | Soltesz et al. | 606/41 |
| 8,585,695 B2 * | 11/2013 | Shih | 606/41 |
| 2001/0007940 A1 | 7/2001 | Tu et al. | |
| 2001/0014780 A1 | 8/2001 | Martin et al. | |
| 2001/0053885 A1 | 12/2001 | Gielen et al. | |
| 2002/0002371 A1 * | 1/2002 | Acker et al. | 606/27 |
| 2002/0019627 A1 | 2/2002 | Maguire et al. | |
| 2002/0022833 A1 | 2/2002 | Maguire et al. | |
| 2002/0026127 A1 | 2/2002 | Balbierz et al. | |
| 2002/0048310 A1 | 4/2002 | Heuser | |
| 2002/0055754 A1 * | 5/2002 | Ranucci et al. | 606/169 |
| 2002/0077643 A1 * | 6/2002 | Rabiner et al. | 606/169 |
| 2002/0169394 A1 | 11/2002 | Eppstein et al. | |
| 2002/0188218 A1 | 12/2002 | Lipman | |
| 2003/0013968 A1 | 1/2003 | Fjield et al. | |
| 2003/0092667 A1 | 5/2003 | Tachibana et al. | |
| 2003/0125726 A1 * | 7/2003 | Maguire et al. | 606/41 |
| 2003/0151417 A1 | 8/2003 | Koen | |
| 2003/0181901 A1 | 9/2003 | Maguire et al. | |
| 2003/0195496 A1 | 10/2003 | Maguire et al. | |
| 2003/0199747 A1 | 10/2003 | Michlitsch et al. | |
| 2003/0199768 A1 | 10/2003 | Cespedes et al. | |
| 2004/0006333 A1 * | 1/2004 | Arnold et al. | 606/15 |
| 2004/0082859 A1 | 4/2004 | Schaer | |
| 2004/0102769 A1 * | 5/2004 | Schwartz et al. | 606/27 |
| 2005/0015079 A1 * | 1/2005 | Keider | 606/27 |
| 2005/0020967 A1 * | 1/2005 | Ono | 604/22 |
| 2005/0096647 A1 | 5/2005 | Steinke et al. | |
| 2005/0215946 A1 | 9/2005 | Hansmann et al. | |
| 2005/0240170 A1 * | 10/2005 | Zhang et al. | 606/27 |
| 2005/0288730 A1 | 12/2005 | Deem et al. | |
| 2006/0009753 A1 | 1/2006 | Fjield et al. | |
| 2006/0052774 A1 * | 3/2006 | Garrison et al. | 606/42 |
| 2006/0058711 A1 * | 3/2006 | Harhen et al. | 601/2 |
| 2006/0084966 A1 | 4/2006 | Maguire et al. | |
| 2006/0173387 A1 * | 8/2006 | Hansmann et al. | 601/2 |
| 2006/0229594 A1 * | 10/2006 | Francischelli et al. | 606/27 |
| 2006/0241442 A1 | 10/2006 | Barthe et al. | |
| 2006/0241739 A1 | 10/2006 | Besselink et al. | |

(56) References Cited

U.S. PATENT DOCUMENTS

| | | |
|---|---|---|
| 2006/0264809 A1 | 11/2006 | Hansmann et al. |
| 2007/0043297 A1 | 2/2007 | Miyazawa |
| 2007/0088346 A1* | 4/2007 | Mirizzi et al. ............... 606/27 |
| 2007/0142831 A1 | 6/2007 | Shadduck |
| 2007/0142879 A1 | 6/2007 | Greenberg et al. |
| 2007/0203479 A1 | 8/2007 | Auth et al. |
| 2007/0222339 A1* | 9/2007 | Lukacs et al. ............... 310/335 |
| 2007/0225619 A1* | 9/2007 | Rabiner et al. ............... 601/2 |
| 2007/0233057 A1 | 10/2007 | Konishi |
| 2007/0282407 A1 | 12/2007 | Demarais et al. |
| 2008/0039745 A1* | 2/2008 | Babaev ............... 601/2 |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0183110 A1 | 7/2008 | Davenport et al. |
| 2008/0195000 A1 | 8/2008 | Spooner et al. |
| 2008/0214966 A1 | 9/2008 | Slayton et al. |
| 2008/0215039 A1 | 9/2008 | Slatkine et al. |
| 2008/0228111 A1* | 9/2008 | Nita ............... 601/3 |
| 2008/0249518 A1* | 10/2008 | Warnking et al. ............... 606/27 |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1* | 12/2008 | Kania et al. ............... 606/21 |
| 2009/0018446 A1* | 1/2009 | Medan et al. ............... 600/439 |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1* | 9/2009 | Demarais et al. ............... 601/3 |
| 2009/0221955 A1* | 9/2009 | Babaev ............... 604/22 |
| 2009/0254078 A1* | 10/2009 | Just et al. ............... 606/33 |
| 2009/0281478 A1 | 11/2009 | Duke |
| 2009/0299360 A1 | 12/2009 | Ormsby |
| 2010/0036293 A1* | 2/2010 | Isola et al. ............... 601/3 |
| 2010/0081933 A1 | 4/2010 | Sverdlik et al. |
| 2010/0091112 A1 | 4/2010 | Veeser et al. |
| 2010/0114082 A1* | 5/2010 | Sharma ............... 606/27 |
| 2010/0125198 A1* | 5/2010 | Thapliyal et al. ............... 600/439 |
| 2010/0130892 A1* | 5/2010 | Warnking ............... 601/3 |
| 2010/0137860 A1* | 6/2010 | Demarais et al. ............... 606/41 |
| 2010/0152625 A1 | 6/2010 | Milo |
| 2010/0168624 A1* | 7/2010 | Sliwa ............... 601/3 |
| 2010/0168649 A1 | 7/2010 | Schwartz et al. |
| 2010/0191112 A1* | 7/2010 | Demarais et al. ............... 600/439 |
| 2010/0198040 A1* | 8/2010 | Friedman et al. ............... 600/374 |
| 2010/0210946 A1 | 8/2010 | Harada et al. |
| 2010/0222851 A1 | 9/2010 | Deem et al. |
| 2010/0228162 A1* | 9/2010 | Sliwa et al. ............... 601/2 |
| 2010/0331686 A1 | 12/2010 | Hossack et al. |
| 2010/0331950 A1 | 12/2010 | Strommer |
| 2011/0009779 A1 | 1/2011 | Romano et al. |
| 2011/0034809 A1 | 2/2011 | Eberle et al. |
| 2011/0066217 A1 | 3/2011 | Diller et al. |
| 2011/0092781 A1 | 4/2011 | Gertner |
| 2011/0092880 A1 | 4/2011 | Gertner |
| 2011/0112400 A1 | 5/2011 | Emery et al. |
| 2011/0178441 A1 | 7/2011 | Tyler |
| 2011/0201973 A1 | 8/2011 | Stephens et al. |
| 2011/0257563 A1 | 10/2011 | Thapliyal et al. |
| 2011/0264086 A1 | 10/2011 | Ingle |
| 2011/0270247 A1 | 11/2011 | Sherman |
| 2011/0282249 A1 | 11/2011 | Tsoref et al. |
| 2012/0016273 A1 | 1/2012 | Diederich |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0123270 A1 | 5/2012 | Klee et al. |
| 2012/0209116 A1 | 8/2012 | Hossack et al. |
| 2012/0215106 A1 | 8/2012 | Sverdlik et al. |
| 2012/0232409 A1 | 9/2012 | Stahmann et al. |
| 2012/0232436 A1* | 9/2012 | Warnking ............... 601/2 |
| 2012/0265227 A1 | 10/2012 | Sverdlik et al. |
| 2012/0268886 A1 | 10/2012 | Leontiev et al. |
| 2012/0283605 A1 | 11/2012 | Lewis, Jr. |
| 2012/0310233 A1 | 12/2012 | Dimmer et al. |
| 2013/0072928 A1* | 3/2013 | Schaer ............... 606/41 |
| 2013/0131668 A1 | 5/2013 | Schaer |
| 2013/0197555 A1 | 8/2013 | Schaer |
| 2013/0204242 A1 | 8/2013 | Sverdlik et al. |
| 2013/0207519 A1* | 8/2013 | Chaggares et al. ............... 310/335 |
| 2013/0211292 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |
| 2013/0267875 A1 | 10/2013 | Thapliyal et al. |
| 2014/0012133 A1 | 1/2014 | Sverdlik et al. |
| 2014/0039477 A1 | 2/2014 | Sverdlik et al. |
| 2014/0088585 A1 | 3/2014 | Hill et al. |
| 2014/0180197 A1 | 6/2014 | Sverdlik et al. |
| 2015/0073400 A1 | 3/2015 | Sverdlik et al. |
| 2016/0113699 A1 | 4/2016 | Sverdlik et al. |

FOREIGN PATENT DOCUMENTS

| | | |
|---|---|---|
| CN | 101820820 | 9/2010 |
| EP | 1384445 | 1/2004 |
| EP | 1424100 | 6/2004 |
| EP | 1799302 | 3/2006 |
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |
| JP | 07-227394 | 8/1995 |
| JP | 09-122139 | 5/1997 |
| JP | 10-248854 | 9/1998 |
| JP | 2008-536562 | 9/2008 |
| JP | 2010-517695 | 5/2010 |
| WO | WO 91/10405 | 7/1991 |
| WO | WO 99/16366 | 4/1999 |
| WO | WO 00/67648 | 10/2000 |
| WO | WO 01/45550 | 6/2001 |
| WO | WO 2004/054448 | 7/2004 |
| WO | WO 2006/022790 | 3/2006 |
| WO | WO 2006/041847 | 4/2006 |
| WO | WO 2006/041881 | 4/2006 |
| WO | WO 2006/042163 | 4/2006 |
| WO | WO 2007/001981 | 1/2007 |
| WO | WO 2007/078997 | 7/2007 |
| WO | WO 2007/115307 | 10/2007 |
| WO | WO 2007/127176 | 11/2007 |
| WO | WO 2008/003058 | 1/2008 |
| WO | WO 2008/098101 | 8/2008 |
| WO | WO 2008/102363 | 8/2008 |
| WO | WO 2010/009473 | 1/2010 |
| WO | WO 2010/118307 | 10/2010 |
| WO | WO 2011/053757 | 5/2011 |
| WO | WO 2011/060200 | 5/2011 |
| WO | WO 2012/052920 | 4/2012 |
| WO | WO 2012/052921 | 4/2012 |
| WO | WO 2012/052922 | 4/2012 |
| WO | WO 2012/052924 | 4/2012 |
| WO | WO 2012/052925 | 4/2012 |
| WO | WO 2012/052926 | 4/2012 |
| WO | WO 2012/052927 | 4/2012 |
| WO | WO 2012/061713 | 5/2012 |
| WO | WO 2013/030743 | 3/2013 |
| WO | WO 2013/111136 | 8/2013 |
| WO | WO 2013/157009 | 10/2013 |
| WO | WO 2013/157011 | 10/2013 |
| WO | WO 2014/188430 | 11/2014 |
| WO | WO 2016/084081 | 6/2016 |

OTHER PUBLICATIONS

Official Action Dated Aug. 29, 2013 From the US Patent and Trademark Office Re. U.S. Appl. No. 13/449,539.

(56) References Cited

OTHER PUBLICATIONS

Invitation to Pay Additional Fees Dated Sep. 3, 2013 From the International Searching Authority Re. Application No. PCT/IL2013/050339.
International Search Report and the Written Opinion Dated Sep. 19, 2013 From the International Searching Authority Re. Application No. PCT/IL2013/050068.
Official Action Dated Sep. 25, 2013 From the US Patent and Trademark Office Re. U.S. Appl. No. 13/462,956.
Lin et al. "Utility of the PlasmaKinetic™ Bipolar Forceps® for Control of the Renal Artery in a Porcine Model", JTUA, 14(3): 118-121, Sep. 2003.
International Search Report and the Written Opinion Dated Oct. 11, 2013 From the International Searching Authority Re. Application No. PCT/IL2013/050341.
International Search Report and the Written Opinion Dated Oct. 29, 2013 From the International Searching Authority Re. Application No. PCT/IL2013/050339.
Notice of Allowance Dated Nov. 7, 2013 From the US Patent and Trademark Office Re. U.S. Appl. No. 13/049,013.
Official Action Dated Dec. 19, 2013 From the US Patent and Trademark Office Re. U.S. Appl. No. 13/049,022.
International Preliminary Report on Patentability Dated May 2, 2013 From the International Bureau of WIPO Re. Application No. PCT/IB2011/054634.
International Preliminary Report on Patentability Dated May 2, 2013 From the International Bureau of WIPO Re. Application No. PCT/IB2011/054635.
International Preliminary Report on Patentability Dated May 2, 2013 From the International Bureau of WIPO Re. Application No. PCT/IB2011/054636.
International Preliminary Report on Patentability Dated May 2, 2013 From the International Bureau of WIPO Re. Application No. PCT/IB2011/054638.
International Preliminary Report on Patentability Dated May 2, 2013 From the International Bureau of WIPO Re. Application No. PCT/IB2011/054639.
International Preliminary Report on Patentability Dated May 2, 2013 From the International Bureau of WIPO Re. Application No. PCT/IB2011/054640.
International Preliminary Report on Patentability Dated May 2, 2013 From the International Bureau of WIPO Re. Application No. PCT/IB2011/054641.
Schwartz "Strategies to Model Efficacy of Hypertension Devices", EuroPCR 2013, The Leading Cardiovascular Course, 24 P., 2013.
Verloop et al. "The Effects of Renal Denervation on Renal Haemodynamics", Interventions for Hypertenison & Heart Failure, Abstracts of EuroPCR & AsiaPCR/SingLIVE 2013, May 21, 2013.
Invitation to Pay Additional Fees Dated Jul. 24, 2013 From the International Searching Authority Re. Application No. PCT/IL2013/050068.
Official Action Dated Jul. 17, 2013 From the US Patent and Trademark Office Re. U.S. Appl. No. 13/049,013.
Notice of Allowance Dated Jun. 21, 2013 From the US Patent and Trademark Office Re. U.S. Appl. No. 13/049,151.
Restriction Official Action Dated Jun. 28, 2013 From the US Patent and Trademark Office Re. U.S. Appl. No. 13/449,539.
Official Action Dated May 8, 2013 From the US Patent and Trademark Office Re. U.S. Appl. No. 13/462,956.
Failla et al. "Sympathetic Tone Restrains Arterial Distensibility of Healthy and Atherosclerotic Subjects", Journal of Hypertension, 17: 1117-1123, 1999.
Grassi et al. "Sympathetic Mechanisms, Organ Damage, and Antihypertensive Treatment", Current Hypertension Report, 13: 303-308, 2011.
Kleinlogel et al. "A Gene-Fusion Strategy for Stoichiometric and Co-Localized Expression of Light-Gated Membrane Proteins", Nature Methods, 8(12): 1083-1091, Dec. 2011.

Lopez et al. "Effects of Sympathetic Nerves on Collateral Vessels in the Limb of Atherosclerosis Primates", Atherosclerosis, 90: 183-188, 1991.
Mangoni et al. "Effect of Sympathectomy on Mechanical Properties of Common Carotid and Femoral Arteries", Hypertension, 30: 1085-1088, 1997.
Olafsson et al. "Ultrasound Current Source Density Imaging", IEEE Transactions on Biomedical Engineering, 55(7): 1840-1848, Jul. 2008.
Swierblewska et al. "An Independent Relationship Between Muscle Sympathetic Nerve Activity and Pulse Wave Velocity in Normal Humans", Journal of Hypertension, 28: 979-984, 2010.
Wikswo Jr. et al. "Magnetic Field of a Nerve Impulse: First Measurements", Science, 208: 53-55, Apr. 4, 1980.
Witte et al. "Imaging Current Flow in Lobster Nerve Cord Using the Acoustoelectric Effect", Applied Physics Letters, 90: 163902-1-163902-3, 2007.
International Search Report and the Written Opinion Dated Feb. 7, 2012 From the International Searching Authority Re. Application No. PCT/IB2011/054641.
International Search Report and the Written Opinion Dated Jun. 22, 2012 From the International Searching Authority Re. Application No. PCT/IB2011/054640.
International Search Report and the Written Opinion Dated Jan. 23, 2012 From the International Searching Authority Re. Application No. PCT/IB2011/054635.
International Search Report and the Written Opinion Dated Jan. 25, 2012 From the International Searching Authority Re. Application No. PCT/IB2011/054636.
International Search Report and the Written Opinion Dated Jan. 27, 2012 From the International Searching Authority Re. Application No. PCT/IB2011/054634.
International Search Report and the Written Opinion Dated Jan. 27, 2012 From the International Searching Authority Re. Application No. PCT/IB2011/054638.
International Search Report and the Written Opinion Dated Jan. 31, 2012 From the International Searching Authority Re. Application No. PCT/IB2011/054639.
Invitation to Pay Additional Fees Dated Apr. 17, 2012 From the International Searching Authority Re. Application No. PCT/IB2011/054640.
Official Action Dated Oct. 24, 2012 From the US Patent and Trademark Office Re. U.S. Appl. No. 13/049,013.
Official Action Dated Jan. 29, 2013 From the US Patent and Trademark Office Re. U.S. Appl. No. 13/049,151.
Restriction Official Action Dated Oct. 5, 2012 From the US Patent and Trademark Office Re. U.S. Appl. No. 13/049,151.
Restriction Official Action Dated Aug. 30, 2012 From the US Patent and Trademark Office Re. U.S. Appl. No. 13/049,013.
Ahmed et al. "Renal Sympathetic Denervation Using an Irrigated Radiofrequency Ablation Catheter for the Management of Drug-Resistant Hypertension", Journal of the American College of Cardiology: Cardiovascular Interventions, JACC, 5(7): 758-765, 2012.
Anonymus "Indication for and Results of Sympathectomy in Patients With Peripheral Vascular Disease", Lumbar Sympathectomy, Poster, 34 P., 2009.
Aoyama et al. "Comparison of Cryothermia and Radiofrequency Current in Safety and Efficacy of Catheter Ablation Within the Canine Coronary Sinus Close to the Left Circumflex Coronary Artery", Journal of Cardiovascular Electrophysiology, 16: 1218-1226, Nov. 2005.
Atherton et al. "Micro-Anatomy of the Renal Sympathetic Nervous System: A Human Postmortem Histologic Study", Clinical Anatomy, p. 1-6, Oct. 4, 2011.
Bailey et al. "Cavitation Detection During Shock-Wave Lithotripsy", Ultrasound in Medicine and Biology, XP027605630, 31(9): 1245-1256, Sep. 1, 2005. Abstract, Fig.1, p. 1246, p. 1247, r-h Col., p. 1249, r-h Col.
Baker et al. "Operative Lumbar Sympathectomy for Severe Lower Limb Ischaemia: Still a Valuable Treatment Option", Annals of the Royal College of Surgeons of England, 76(1): 50-53, Jan. 1994.

(56) References Cited

OTHER PUBLICATIONS

Bharat et al. "Monitoring Stiffness Changes in Lesions After Radiofrequency Ablation at Different Temperatures and Durations of Ablation", Ultrasound in Medicine & Biology, 31(3): 415-422, 2005.
Blankestijn et al. "Renal Denervation: Potential Impact on Hypertension in Kidney Disease?", Nephrology, Dialysis, Transplantation, 26(9): 2732-2734, Apr. 19, 2011.
Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.
Brandt et al. "Renal Sympathetic Denervation Reduces Left Ventricular Hypertrophy and Improves Cardiac Function in Patients With Resistant Hypertension", Journal of the American College of Cardiology, 59(10): 901-909, 2012.
Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.
Brinton et al. "Externally Focused Ultrasound for Sympathetic Renal Denervation", WAVE I First-In-Man Study, Kona Medical Inc., PowerPont Presentation, TCT 2012, 15 P., 2012.
Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.
Campese et al. "Sympathetic Renal Innervation and Resistant Hypertension", International Journal of Hypertension, 2011(Art.ID 814354): 1-6, 2011.
Copty et al. "Localized Heating of Biological Media Using A 1-W Microwave Near-Field Probe", IEEE Transactions on Microwave Theory and Techniques, 52(8): 1957-1963, Aug. 2004.
Copty et al. "Low-Power Near-Field Microwave Applicator for Localized Heating of Soft Matter", Applied Physics Letters, 84(25): 5109-5111, Jun. 21, 2004.
Damianou et al. "Dependence of Ultrasonic Attenuation and Absorpteion in Dog Soft Tissues on Temperature and Thermal Dose", Journal of the Acoustical Society of America, 102(1): 628-634, Jul. 1997.
Davies et al. "First-in-Man Safety Evaluation of Renal Denervation for Chronic Systolic Heart Failure: Primary Outcome From REACH-Pilot Study", International Journal of Cardiology, 162: 189-192, 2013.
Deneke et al. "Histopathology of Intraoperatively Induced Linear Radiofrequency Ablation Lesions in Patients With Chronic Atrial Fibrillation", European Heart Journal, 26: 1797-1803, 2005.
DiBona "Neural Control of Renal Function: Cardiovascular Implications", Hypertension, 13: 539-548, 1989.
DiBona "Neural Control of the Kidney: Past, Present, and Future", Hypertension, 41: 621-624, Dec. 16, 2002.
DiBona "Physiology in Perspective: The Wisdom of the Body. Neural Control of the Kidney", American Journal of Physiology, Regulatory, Integrative and Comparative Physiology, 289(3): R633-R641, Sep. 2005.
DiBona et al. "Differentiated Sympathetic Neural Control of the Kidney", American Journal of Physiology, 271: R84-R90, 1996.
DiBona et al. "Translational Medicine: The Antihypertensive Effect of Renal Denervation", American Journal of Physiology, Regulatory, Integrative and Comparative Physiology, 298(2): R245-R253, Feb. 2010.
Diederich et al. "Induction of Hyperthermia Using an Intracavitary Multielement Ultrasonic Applicator", IEEE Transactions on Biomedical Engineering, 36(4): 432-438, Apr. 1989.
Esler "The 2009 Carl Ludwig Lecture: Pathophysiology of the Human Sympathetic Nervous System in Cardiovascular Diseases: The Transition From Mechanisms to Medical Management", Journal of Applied Physiology, 108: 227-237, 2010.

Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.
Fischell PeriVascular Renal Denervation (PVRD™), Ablative Solutions Inc., TransCatheter Therapeutics Meeting, Miami, FL, USA, Oct. 24, 2012, PowerPoint Presentation, 14 P., Oct. 2012.
Fort Wayne Metals "HHS Tube", Fort Wayne Metals Research Products Corporation, 2 P., 2009.
Fujikura et al. "Effects of Ultrasonic Exposure Parameters on Myocardial Lesions Induced by High-Intensity Focused Ultrasound", Journal of Ultrasound Medicine, 25: 1175-1186, 2006.
Glazier et al. "Laser Balloon Angioplasty Combined With Local Intrcoronary Heparin Therapy: Immediate and Short-Term Follow-Up Results", American Heart Journal, 134: 266-273, 1997.
Goswami "Renal Denervation: A Percutaneous Therapy for HTN", Prairie Heart Institute, Synvacor, The VEINS: Venous Endovascular Interventions Strategies, Chicago, USA, 42 P., 2012.
Granada et al. "A Translational Overview for the Evaluation of Peri-Renal Denervation Technologies", Cardiovascular Research Foundation, Columbai University Medical Center, New York, USA, Alizee Pathology, 25 P., 2011.
Griffiths et al. "Thoraco-Lumbar Splanchnicectomy and Sympathectomy. Anaesthetic Procedure", Anaesthesia, 3(4): 134-146, Oct. 1948.
Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.
Hering et al. "Renal Denervation in Moderate to Severe CKD", Journal of the American Society of Nephrology, 23: 1250-1257, 2012.
Hering et al. "Substantial Reduction in Single Sympathetic Nerve Firing After Renal Denervation in Patients With rRsistant. Hypertension", Hypertension, 61: 1-14, Nov. 19, 2012.
Janssen et al. "Role of Afferent Renal Nerves in Spontaneous Hypertension in Rats", Hypertension, 13: 327-333, 1989.
Joner "Histopathological Characterization of Renal Arteries After Radiofrequency Catheter Based Sympathetic Denervation in a Healthy Porcine Model", Deutsches Herzzentrum M?nchen, Technische Universit?t M?nchen, PowerPoint Presentation, TCT 2012, 15 P., 2012.
Katholi "Renal Nerves in the Pathogenesis of Hypertension in Experimental Animals and Humans", American Journal of Physiology, 245: F1-F14, 1983.
Katholi et al. "Intrarenal Adenosine Produces Hypertension by Activating the Sympathetic Nervous System Via the Renal Nerves in the Dog", Journal of Hypertension, 2: 349-359, 1984.
Katholi et al. "Renal Nerves in the Maintenance of Hypertension: A Potential Therapeutic Target", Current Hypertension Reports, 12(3): 196-204, Jun. 2010.
Kline et al. "Functional Reinnervation and Development of Supersensitivity to NE After Renal Denervation in Rats", American Journal of Physiology, 238: R353-R358, 1980.
Kolh "Carotid Denervation by Adventitial Stripping: A Promising Treatment of Carotid Sinus Syndrome?", European Journal of Vascular and Endovascular Surgery, 39(2): 153-154, Feb. 2010.
Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.
Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.
Lambert et al. "Redo of Percutaneous Renal Denervation in a Patient With Recurrent Resistant Hypertension After Primary Treatment Success", Catheterization and Cardiovascular Interventions, p. 1-11, 2012.
Lele "Effects of Focused Ultrasonic Radiation on Peripheral Nerve, With Observations on Local Heating", Experimental Neurology, 8: 47-83, 1963.
Lemoine et al. "Amputations and Sympathectomy in Peripheral Vascular Disease of the Lower Extremity. Experience With 180 Patients", Journal of the National Medical Association, 61(3): 219-221, May 1969.

(56) References Cited

OTHER PUBLICATIONS

Li et al. "Acoustic Proximity Ranging in the Presence of Secondary Echoes", IEEE Transactions on Instrumentation and Measurement, XP011102759, 52(5): 1593-1605, Oct. 1, 2003. p. 1593.

Liu et al. "A Helical Microwave Antenna for Welding Plaque During Balloon Angioplasty", IEEE Transactions on Microwave Theory and Techniques, 44(10): 1819-1831, Oct. 1996.

Mabin et al. "First Experience With Endovascular Ultrasound Renal Denervation for the Treatment of Resistant Hypertension", EuroIntervention, 8: 57-61, 2012.

Mahfoud et al. "Effect of Renal Sympathetic Denervation on Glucose Metabolism in Patients With Resistant Hypertension: A Pilot Study", Circulation, 123: 1940-1946, 2011.

Mahfoud et al. "Is There a Role for Renal Sympathetic Denervation in the Future Treatment of Resistant Hypertension?", Future Cardiology, 7(5): 591-594, 2011.

Mahfoud et al. "Renal Hemodynamics and Renal Function After Catheter-Based Renal Sympathetic Denervation in Patients With Resistant Hypertension", Hypertension, 60: 419-424, 2012.

Makris et al. "Resistant Hypertension Workup and Approach to Treatment", International Journal of Hypertension, 2011(Art. ID598694): 1-10, 2011.

Manasse et al. "Clinical Histopathology and Ultrstructural Analysis of Myocardium Following Microwave Energy Ablation", European Journal of Cardio-Thoracic Surgery, 23: 573-577, 2003.

Martin et al. "Premise, Promise, and Potential Limitations of Invasive Devices to Treat Hypertension", Current Cardiology Reports, 13(1): 86-92, Feb. 2011.

Mazor "Efficacy of Renal Denervation Is Positively Impacted by Longitudinal Treatments", Vessix Vascular Inc., PowerPoint Presentation, TCT 2012, 20 P., 2012.

Mogil et al. "Renal Innervation and Renin Activity in Salt Metabolism and Hypertension", American Journal of Physiology, 216(4): 693-697, Apr. 1969.

Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.

Ohkubo et al. "Histological Findings After Angioplasty Using Conventional Balloon, Radiofrequency Thermal Balloon, and Stent for Experimental Aortic Coarctation", Pediatrics International, 46: 39-47, 2004.

Ong et al. "Successful Treatment of Resistant Hypertension With Percutaneous Renal Denervation Therapy", Heart, 98(23): 1754-1755, Dec. 2012.

Ormiston "One Shot (Covidien)", Maya Medical, Auckland, New Zealand, PowerPoint Presentation.

Ormiston et al. "First-in-Human Use of the OneShot™ Renal Denervation System From Covidien", EuroIntervention, 8: 1090-1094, 2013.

Page et al. "The Effect of Renal Denervation on Patients Suffering From Nephritis", The Journal of Clinical Investigation, 14(4): 443-458, Jul. 1935.

Papademetriou et al. "Renal Sympathetic Denervation for the Treatment of Difficult-to-Control or Resistant Hypertension", International Journal of Hypertension, 2011(Art.ID196518): Jan. 1-8, 2011.

Para Tech Coating "Parylene Properties", Para Tech Coating Inc., 1 P.

Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.

Prochnau et al. "Catheter-Based Renal Denervation for Drug-Resistant Hypertension by Using a Standard Electrophysiology Catheter", EuroIntervention, 7: 1077-1080, 2012.

Prochnau et al. "Efficacy of Renal Denervation With a Standard EP Catheter in the 24-h Ambulatory Blood Pressure Monitoring—Long-Term Follow-Up", International Journal of Cardiology, 157(3): 447-448, Jun. 14, 2012.

Quinn "Pre-Eclampsia and Partial Uterine Denervation", Medical Hypotheses, 64(3): 449-454, 2005. Abstract.

Rappaport "Treating Cardiac Disease With Catheter-Based Tissue Heating", IEEE Microwave Magazine, p. 57-64, Mar. 2002.

Rothman "FIM Evaluation of a New, Multi-Electrode RF System for Renal Denervation (Medtronic)", Medtronic Inc., PowerPoint Presentation, 8 P., 2012.

Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.

Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.

Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.

Sanni et al. "Is Sympathectomy of Benefit in Critical Leg Ischaemia Not Amenable to Revascularisation?", Interactive CardioVascular and Thoracic Surgery, 4: 478-483, 2005.

Scheinert "Cardiosonic TIVUS™ Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.

Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.

Schlaich et al. "Renal Sympathetic-Nerve Ablation for Uncontrolled Hypertension", New England Journal of Medicine, 361(9): 932-934, Aug. 27, 2009.

Sievert et al. "Catheter-Based Technology Alternatives for Renal Denervation", CardioVascular Center Frankfurt, Germany, TCT 2012, Miami, FL, USA, Oct. 22-26, 2012, PowerPoint Presentation, 35 P., Oct. 2012.

Souchon et al. "Monitoring the Formation of Thermal Lesions With Heat-Induced Echo-Strain Imaging: A Feasibility Study", Ultrasound in Medicine & Biology, 31(2): 251-259, 2005.

Stefanadis "Vincristine Local Delivery for Renal Artery Denervation", Athens, Greece, PowerPoint Presentation, TCT 2012, 21 P., 2012.

Steigerwald et al. "Morphological Assessment of Renal Arteries After Radiofrequency Catheter-Based Sympathetic Denervation in a Porcine Model", Journal of Hypertension, 30(11): 2230-2239, Nov. 2012.

Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.

Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.

Szabo "Diagnostic -Ultrasound Imaging: Inside Out", Academic Press Series in Biomedical Engineering, 2004. Book: Diagnostic Ultrasound Imaging Inside Out—Bronzino ; Academic Press Series in Biomedical Engineering ,Joseph Bronzino, Series Editor ; Trinity College—Hartford, Connecticut "Diagnostic Ultrasound Imaging Inside Out", Academic Press Series in Biomedical Engineering, 2004.

Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.

(56) References Cited

OTHER PUBLICATIONS

Toorop et al. "Clinical Results of Carotid Denervation by Adventitial Stripping in Caotid Sinus Syndrome", Europan Journal of Vascular and Endovascular Syndrome, 39: 146-152, 2010.
Tyreus et al. "Two-Dimensional Acoustic Attenuation Mapping of High-Temperature Interstitial Ultrasound Lesions", Physics in Medicine and Biology, 49: 533-546, 2004.
Virmani "Translation Medicine and Renal Denervation: Pre-Clinical Animal Models and Histoanatomy", CVPath Institute, Gaithersburg, MD, USA, PowerPoint Presentation.
Voskuil et al. "Percutaneous Renal Denervation for the Treatment of Resistant Essential Hypertension; The First Dutch Experience", Netherlands Heart Journal, 19(7-8): 319-323, Aug. 2011.
Warwick et al. "Trackless Lesions in Nervous Tissues Produced by High Intensity Focused Ultrsound (High-Frequency Mechanical Waves)", Journal of Anatomy, 102(3): 387-405, 1968.
Wilcox "Resistant Hypertension and the Role of the Sympathetic Nervous System", Medtronic, 30 P.
Williams et al. "Laser Energy Source in Surgical Atrial Fibrillation Ablation: Preclinical Experience", The Annals of Thoracic Surgery, 82: 2260-2264, 2006.
Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.
Wolf-De Jonge et al. "25 Years of Laser Assisted Vascular Anastomosis (LAVA): What Have We Learned?", European Journal of Vascular and Endovascular Surgery, 27(5): 466-476, May 2004.
Worthington et al. "Changes in Ultrasound Properties of Porcine Kidney Tissue During Heating", Ultrasound in Medicine & Biology, 27(5): 673-682, 2001.
Worthington et al. "Ultrasound Properties of Human Prostate Tissue During Heating", Ultrsound in Medicine & Biology, 28(10): 1311-1318, 2002.
Xu et al. "Experimental Nerve Thermal Injury", Brain, 117: 375-384, 1994.
Applicant-Initiated Interview Summary Dated Jan. 24, 2014 From the US Patent and Trademark Office Re. U.S. Appl. No. 13/449,539.
Communication Pursuant to Article 94(3) EPC Dated Jun. 10, 2014 From the European Patent Office Re. Application No. 117822476.3.
Communication Pursuant to Article 94(3) EPC Dated Jun. 10, 2014 From the European Patent Office Re. Application No. 11784782.2.
Communication Pursuant to Article 94(3) EPC Dated Apr. 14, 2014 From the European Patent Office Re. Application No. 11782221.3.
Communication Pursuant to Article 94(3) EPC Dated Sep. 26, 2014 From the European Patent Office Re. Application No. 11782222.1.
Communication Pursuant to Rules 70(2) and 70a(2) EPC Dated Mar. 28, 2014 From the European Patent Office Re. Application No. 11833950.6.
Communication Under Rule 71(3) EPC Dated Apr. 24, 2014 From the European Patent Office Re. Application No. 11782223.9.
International Preliminary Report on Patentability Dated Aug. 7, 2014 From the International Bureau of WIPO Re. Application No. PCT/IL2013/050068.
Invitation Pursuant to Rule 137(4) EPC Dated Apr. 4, 2014 From the European Patent Office Re. Application No. 11785792.0.
Invitation Pursuant to Rule 137(4) EPC Dated Apr. 8, 2014 From the European Patent Office Re. Application No. 11782222.1.
Invitation Pursuant to Rule 137(4) EPC Dated Apr. 10, 2014 From the European Patent Office Re. Application No. 11782476.3.

Invitation to Pay Additional Fees Dated Sep. 4, 2014 From the International Searching Authority Re. Application No. PCT/IL2014/050457.
Notice of Allowance Dated Oct. 6, 2014 From the US Patent and Trademark Office Re. U.S. Appl. No. 13/880,061.
Office Action Dated Jul. 30, 2014 From the State Intellectual Property Office of the People's Republic of China Re. Application No. 201180060741.3 and Its Summary in English.
Official Action Dated Oct. 7, 2014 From the US Patent and Trademark Office Re. U.S. Appl. No. 13/880,109.
Official Action Dated Sep. 10, 2014 From the US Patent and Trademark Office Re. U.S. Appl. No. 14/049,238.
Official Action Dated Mar. 20, 2014 From the US Patent and Trademark Office Re. U.S. Appl. No. 13/449,539.
Official Action Dated Apr. 23, 2014 From the US Patent and Trademark Office Re. U.S. Appl. No. 13/880,061.
Restriction Official Action Dated Jul. 7, 2014 From the US Patent and Trademark Office Re. U.S. Appl. No. 14/049,238.
Search Report Dated Jul. 30, 2014 From the State Intellectual Property Office of the People's Republic of China Re. Application No. 201180060741.3.
Supplementary European Search Report Dated Mar. 12, 2014 From the European Patent Office Re. Application No. 11833950.6.
Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.
Diederich et al. "Catheter-Based Ultrasound Devices and MR Thermal Monitoring for Conformal Prostate Thermal Therapy", 30th Annual International IEEE EMBS Conference, Vancouver, British Columbia, Canada, Aug. 20-24, 2008, p. 3664-3668, 2008.
Diederich et al. "Ultrasound Technology for Hyperthermia", Ultrasound in Medicine & Biology, 25(6): 871-887, 1999.
Donoho et al. "Stable Recovery of Sparse Overcomplete Representations in the Presence of Noise", IEEE Transactions on Information Theory, 52(1): 1-42, Jan. 2006.
Gander et al. "Least-Squares Fitting of Circles and Ellipses", BIT Numerical Mathematics, 34(4): 558-578, Dec. 1994.
Holdaas et al. "Modulation of Reflex Renal Vasoconstriction by Increased Endogenous Renal Prostaglandin Synthesis", The Journal of Pharmacology and Experimental Therapeutics, 232(3): 725-731, 1985.
Lafon "Miniature Devices for Minimally Invasive Thermal Ablation by High Intensity Ultrasound", Cargese Workshop 2009, University of Lyon, Prance, INSERM U556, Presentation, 39 P., 2009.
Reddy "Sound Intervention", Mount Sinai School of Medicine, MSSM, Presentation, 19 P., 2012.
Tibshirani "Regression Shrinkage and Sciction Via the Lasso: A Retrospective", Journal of the Royal Statistical Society, Series B: Statistical Methodology, 73(Pt.3): 273-282, 2011.
Tibshirani "Regression Shrinkage and Selection Via the Lasso", Journal of the Royal Statistical Society, Series B: Methodological, 58(1): 267-288, 1996.
Zeller "Percutaneous Renal Denervation System. The New Ultrasound Solution for the Mangament of Hypertension", Paradise Ultrasound Denervation System, ReCor Medical, 27 P., 2013.
Applicant-Initiated Interview Summary Dated Jan. 21, 2015 From the US Patent and Trademark Office Re. U.S. Appl. No. 13/449,539.
Communication Pursuant to Article 94(3) EPC Dated Nov. 4, 2014 From the European Patent Office Re. Application No. 11833950.6.
Communication Pursuant to Article 94(3) EPC Dated Oct. 30, 2014 From the European Patent Office Re. Application No. 11782221.3.
International Preliminary Report on Patentability Dated Oct. 30, 2014 From the International Bureau of WIPO Re. Application No. PCT/IL2013/050339.
International Preliminary Report on Patentability Dated Oct. 30, 2014 From the International Bureau of WIPO Re. Application No. PCT/IL2013/050341.
International Search Report and the Written Opinion Dated Nov. 20, 2014 From the International Searching Authority Re. Application No. PCT/IL2014/050457.
Notice of Allowance Dated Jan. 8, 2015 From the US Patent and Trademark Office Re. U.S. Appl. No. 13/880,061.

(56) References Cited

OTHER PUBLICATIONS

Notification of Office Action and Search Report Dated Dec. 1, 2014 From the State Intellectual Property Office of the People's Republic of China Re. Application No. 201180060862.8.
Official Action Dated Dec. 3, 2014 From the US Patent and Trademark Office Re. U.S. Appl. No. 13/462,956.
Official Action Dated Nov. 5, 2014 From the US Patent and Trademark Office Re. U.S. Appl. No. 13/049,022.
Official Action Dated Feb. 6, 2015 From the US Patent and Trademark Office Re. U.S. Appl. No. 14/190,113.
Restriction Official Action Dated Nov. 17, 2014 From the US Patent and Trademark Office Re. U.S. Appl. No. 13/880,066.
Restriction Official Action Dated Feb. 27, 2015 From the US Patent and Trademark Office Re. U.S. Appl. No. 13/905,224.
Restriction Official Action Dated Oct. 30, 2014 From the US Patent and Trademark Office Re. U.S. Appl. No. 13/880,083.
Translation Dated Mar. 12, 2015 of Notification of Office Action and Search Report Dated Dec. 1, 2014 From The State Intellectual Property Office of the People's Republic of China Re. Application No. 201180060862.8.
Cardiosonic "Cardiosonic New Applications", Cardiosonic, p. 1-20, Mar. 2014.
Cardiosonic "Histological Map of Swine Pulmonary Arteries", Cardiosonic, Animal #223, Mar. 26, 2014.
Cardiosonic "Histological Map of Swine Pulmonary Arteries", Cardiosonic, Animal #234, Mar. 18, 2014.
Cardiosonic "Histological Map of Swine Pulmonary Arteries", Cardiosonic, Animal #234, Mar. 26, 2014.
Cardiosonic "Histopathology Report", Cardiosonic, 2 P., Dec. 26, 2013.
Cardiosonic "PA/Trachea—Feedback Provisional", Cardiosonic, 5 P, Jun. 9, 2014.
Drake et al. "Problematic Anatomical Sites Around the Pulmonary Artery", Gray's Anatomy for Students, 9 P., 2004.
Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.
Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.
Schelegle et al. "Vagal Afferents Contribute to Exacerbates Airway Responses Following Ozone and Allergen Challenge", Respiratory Physiology & Neurobiology, 181(3): 277-285, May 31, 2012.
Notice of Non-Compliant Amendment Dated Sep. 23, 2015 From the US Patent and Trademark Office Re. U.S. Appl. No. 13/880,124.
Official Action Dated Aug. 5, 2015 From the US Patent and Trademark Office Re. U.S. Appl. No. 13/905,224.
Official Action Dated Sep. 11, 2015 From the US Patent and Trademark Office Re. U.S. Appl. No. 13/880,066.
Official Action Dated Aug. 14, 2015 From the US Patent and Trademark Office Re. U.S. Appl. No. 13/449,539.
Official Action Dated Sep. 25, 2015 From the US Patent and Trademark Office Re. U.S. Appl. No. 14/190,113.
Reason for Rejection Dated Aug. 20, 2015 From the Japanese Patent Office Re. Application No. 2013 534435.
Ali et al. "Signal Processing Overview of Ultrasound Systems for Medical Imaging", Texas Instruments White Paper, SPRAB12: Nov. 1-27, 2008.
Bambi et al. "Real-Time Digital Processing of Doppler Ultrasound Signals", IEEE International Conference on Acoustics, Speech, and Signal Processing, Proceedings, (ICASSP '05), (5): v/977-v/980, Mar. 23-23, 2005.
Schnyder et al. "Common Femoral Artery Anatomy Is Influenced by Demographics and Comorbidity: Implications for Cardiac and Peripherial Invasive Studies", Catheterization and Cardiovascular Interventions, 53(3): 289-295, Jul. 2001.
Shung "Doppler Flow Measurements", Diagnostic Ultrasound—Imaging and Blood Flow Measurements, Chap.5:103-104, 2006.
Wu et al. "A Quality Control Program for MR-Guided Focused Ultrasound Ablation Therapy", Journal of Applied Clinical Medical Physics, 3(2): 162-167, Spring 2002.
Communication Pursuant to Article 94(3) EPC Dated Jul. 27, 2016 From the European Patent Office Re. Application No. 11782222.1.
Decision of Rejection Dated Apr. 28, 2016 From the Japanese Patent Office Re. Application No. 2013-534435 and Its Machine Translation in English.
International Preliminary Report on Patentability Dated Dec. 3, 2015 From the International Bureau of WIPO Re. Application No. PCT/IL2014/050457.
International Search Report and the Written Opinion Dated May 2, 2016 From the International Searching Authority Re. Application No. PCT/IL2015/051145.
Invitation Pursuant to Rule 137(4) EPC Dated Mar. 21, 2016 From the European Patent Office Re. Application No. 11782222.1.
Invitation to Pay Additional Fees Dated Mar. 4, 2016 From the International Searching Authority Re. Application No. PCT/IL2015/051145.
Official Action Dated Jul. 126, 2016 From the U.S. Appl. No. 13/880,124.
Translation Dated Nov. 18, 2015 of Notice of Reason for Rejection Dated Aug. 25, 2015 From the Japanese Patent Office Re. Application No. 2013-534435.

* cited by examiner

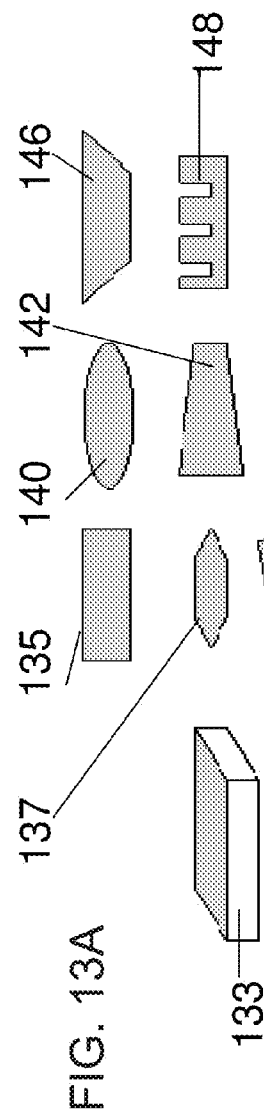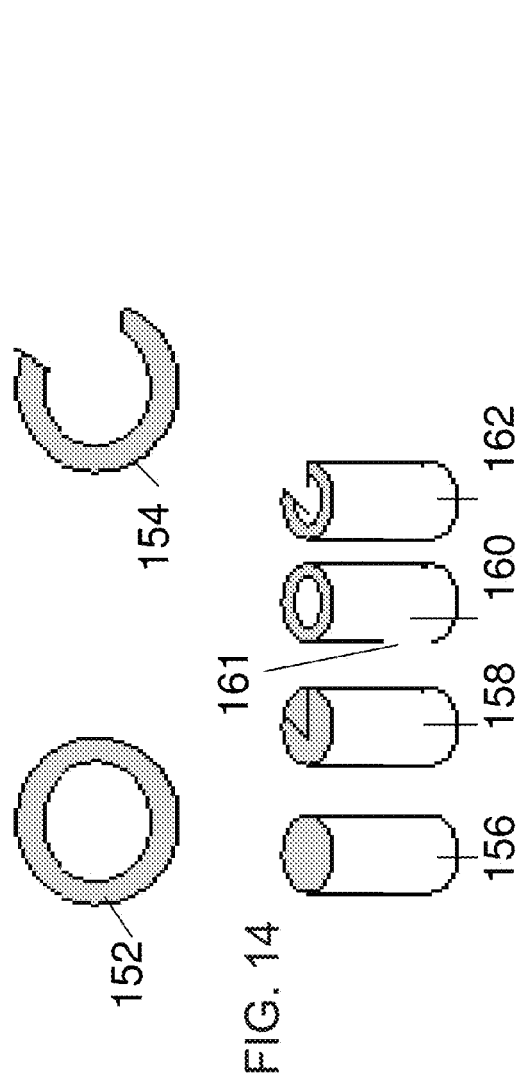
FIG. 13A
FIG. 13B
FIG. 14

ULTRASOUND TRANSCEIVER AND COOLING THEREOF

RELATED APPLICATIONS

This application is a National Phase of PCT Patent Application No. PCT/IB2011/054641 having International filing date of Oct. 18, 2011, which is a continuation-in-part (CIP) of pending U.S. patent application Ser. No. 13/049,022 filed on Mar. 16, 2011, and which claims the benefit of priority under 35 USC §119(e) of U.S. Provisional Patent Application No. 61/393,947 filed on Oct. 18, 2010.

U.S. patent application Ser. No. 13/049,022 claims the benefit of priority under 35 USC §119(e) of U.S. Provisional Patent Application No. 61/393,947 filed on Oct. 18, 2010.

The contents of the above applications are all incorporated by reference as if fully set forth herein in their entirety.

The present application claims priority from U.S. Provisional Patent Application No. 61/393,947 filed Oct. 18, 2010, and U.S. patent application Ser. No. 13/049,022 filed Mar. 16, 2011.

The present application is related to co-filed, co-pending and co-assigned PCT patent applications entitled:

"Therapeutics Reservoir", relating to relates to a method of drug delivery and, more particularly to a method for trapping drugs to form a drug reservoir in tissue.

"Ultrasound Emission element", showing for example, an apparatus for generating relatively high efficiency ultrasound;

"an ultrasound transceiver and uses thereof", showing for example, a method for feedback and control of the ultrasonic transceiver;

"An Ultrasound Transceiver and Control of A Thermal Damage Process", showing for example, a method of signal processing to obtain the primary echo;

"tissue treatment", PCT application number IB2011/054640 by Ariel Sverdlik, Iris Szwarcfiter and Or Shabtay, showing for example, a method of selectively targeting and treating tissues using ultrasound; and "separation device for ultrasound element", PCT application number IB2011/054638 by Ariel Sverdlik and Or Shabtay, showing for example, a device to prevent the transceiver from touching the blood vessel wall.

The disclosures of each of the above are incorporated herein by reference.

FIELD AND BACKGROUND OF THE INVENTION

The present invention relates to an ultrasound transceiver device and cooling thereof and, more particularly, but not exclusively to the cooling of such a transceiver device within a small vessel which may be filled with fluid, such as a blood vessel or other body lumen.

Sverdlik et al, in PCT/IL2008/000234, filed Feb. 21, 2008 disclose a method of using ultrasonic energy for surgical procedures. In a procedure for stabilizing blood vessel wall abnormality, ultrasonic heating is carried out of at least a portion of the blood vessel wall having the abnormality. A parameter is monitored relating to a property of at least a portion of the heated portion of the blood vessel wall; and heating is stopped when the monitored parameter changes by a predetermined factor or after the monitored parameter changes at a slow enough rate.

Maguire and Peacock, in EP 1769759 disclose an air backed ultrasonic transceiver. Specifically they disclose an ultrasound transceiver mounted onto a delivery member, such as the elongate body of a catheter shaft, without a support structure bridging between a separation area between the transceiver and the shaft. Mounting flanges extend from either end of the transceiver and are mounted at first and second locations along the catheter shaft such that the transceiver is not in mechanical contact with the catheter shaft between those mounting locations to provide for air backing between the transceiver and the catheter shaft so as to isolate ultrasound transmission radially away from the catheter shaft and toward the tissue surrounding the shaft. In Maguire and Peacock, sealing of the transceiver ensures that body fluids such as blood do not displace the air.

An ultrasound transceiver can in principle be used to provide a high power ultrasound beam that can thermally damage tissues. However the transformation of electrical energy into ultrasound is inefficient and considerable heat is generated at the transceiver. The heat needs to be safely dissipated without causing damage to the blood vessel itself, and standard heat sink structures cannot be used in blood flow because heat exchange fins can damage platelets and cause clotting. In general the transceiver may be expected to heat the artery wall as well as the more distant features it is intended to damage thermally.

Furthermore, ultrasound transceivers are typically ceramics with piezoelectric properties. Ceramics have low thermal conductivity and thus operation at high power causes relatively large heat differentials across the transceiver which often causes cracking.

SUMMARY OF THE INVENTION

The present embodiments may provide a transceiver which carries out tissue damage using an unfocused beam from an extended surface of the transceiver. The beam heats surrounding fluid and sets up a chimney effect which then serves to cool the transceiver surface.

The use of higher frequencies, in excess of 8 Megahertz, allows for thinner transceivers to be used, which reduces the likelihood that large heat differentials will form or cause cracking. The thicknesses used are between 100-200 microns, and higher energies result from the higher frequencies used. The ultrasonic energy may be focused or unfocussed.

According to one aspect of the present invention there is provided an ultrasonic transceiver device for producing ultrasonic beams, comprising a body vibratable at ultrasonic frequencies and an extensive surface for beam emanation, the device configured to produce an unfocused power beam for thermal tissue damage, the unfocused power beam being produced by vibration over the body of the transceiver and emanating from said extensive surface, whereby the extensive surface becomes subject to convective cooling when immersed in a fluid by a chimney effect set up by said unfocused beam.

The device may be mounted on a PCB, wherein trenches are constructed in the PCB for fluid flow to enhance said cooling.

The device may comprise a pump unit for actively pumping liquid around said transceiver.

In an embodiment, said ultrasonic transceiver device comprises a piezoelectric element and wherein said vibratable body is a body of said piezoelectric element.

The device may comprise a gas-filled gap between said transceiver and said PCB.

In an embodiment, said gas-filled gap is unsealed and wherein surface tension retains air within said gap when said device is immersed in fluid.

The device may comprise conductive connections to the PCB across the gas-filled gap, wherein said conductive connections provide thermal linkage between said transceiver and said PCB, thereby enabling the PCB to act as an additional heat dissipation surface for said device.

The device may be located at a circumferential wall of a catheter or at the end of said catheter, and thermally connected to a heat sink that is located within the catheter and/or at the circumferential wall of the catheter or in the blood flow.

The device may be located at a circumferential wall of a catheter or at the end of said catheter, and wherein saline is pumped down the catheter to provide additional fluid flow around the transceiver and/or around the heat sink.

The device may comprise a temperature sensor located in association with said transceiver.

In an embodiment, said temperature sensor is located downstream of said transceiver in a flow direction of liquid in a vessel within which said device is placed, thereby to measure temperature of liquid that has passed said extensive surface.

The device may comprise a controller for providing said power beam in a duty cycle, said controller being configured to modify said duty cycle and/or applied power in response to changes in temperature indicated by said temperature sensor.

In an embodiment, said controller is configured to modify said duty cycle to control said surface to remain within a range of 40° C. to 50° C., or at 44° C.

The device may be controllable to stop said power beam when a temperature sensed by said sensor reaches or exceeds a predetermined safety threshold.

The device may be located at the end of a catheter, and may comprise a temperature sensor located in association with said transceiver, wherein saline is pumped down the catheter to provide fluid flow around the transceiver and wherein a rate of pumping is controlled according to changes in temperature sensed by said temperature sensor.

In an embodiment, said controller is configured to modify said rate of pumping to control said surface to remain within a range of 40° C. to 50° C., or at 44° C.

In an embodiment, said power beam is provided at a frequency of at least 8 Megahertz, and said vibratable body has a thickness not exceeding 0.3 millimeters, thereby to increase heat transfer from the element.

An embodiment may comprise a distancing mechanism for positioning said transceiver at least a minimal distance away from the cavity wall.

An embodiment may comprise a controllable valve openable into a body lumen for controlling fluid flow about said device.

An embodiment may comprise a thermoelectric, or Tec, cooler device to actively enhance cooling.

The device may include metal channels in a PCB, to allow liquid flow to cool the device.

A distancing device may distance the transceivers from a vessel wall, to allow liquid flow in between the device and wall, both for cooling the device and the wall. In this way the vessel wall is not damaged by the ultrasound beam.

According to a further aspect of the present invention there is provided an ultrasonic transceiver device for producing ultrasonic beams, comprising a body vibratable at ultrasonic frequencies and a surface for beam emanation, the device configured to produce an unfocused power beam over an extent of said surface for thermal tissue damage, the unfocused power beam being at a frequency of at least 8 Megahertz.

The device may have a thickness below 0.3 millimeters or a thickness of 0.15 millimeters, thereby to increase heat transfer from the element.

According to a further aspect of the present invention there is provided an ultrasonic transceiver device for producing ultrasonic beams, comprising a body vibratable at ultrasonic frequencies, the device configured to produce a focused power beam for thermal tissue damage, the focused power beam being produced by vibration over the body of the transceiver whereby a surface of said transceiver becomes subject to convective cooling when immersed in a fluid by a chimney effect set up by said focused beam.

According to a yet further aspect of the present invention there is provided an ultrasonic transceiver device for producing ultrasonic beams, comprising a body vibratable at ultrasonic frequencies and an extensive surface for beam emanation, the device configured to produce an unfocused power beam for thermal tissue damage, the unfocused power beam being produced by vibration over the body of the transceiver and emanating from said extensive surface, the device further comprising a heatsink thermally coupled to said body for dissipating heat from said device.

In an embodiment, said heatsink comprises braiding along a wall of a catheter to which said device is attached.

According to a further aspect of the present invention there is provided an ultrasonic transceiver device for producing ultrasonic beams, comprising a body vibratable at ultrasonic frequencies and an extensive surface for beam emanation, the device configured to produce an unfocused power beam for thermal tissue damage or ablation, the unfocused power beam being produced by vibration over the body of the transceiver and emanating from said extensive surface, the device further comprising a thermo-electric cooler device thermally coupled to said body for cooling said body.

According to a further aspect of the present invention there is provided an ultrasonic transceiver device for producing ultrasonic beams, comprising a body vibratable at ultrasonic frequencies and an extensive surface for beam emanation, the device configured to produce an unfocused power beam for thermal tissue damage, the unfocused power beam being produced by vibration over the body of the transceiver and emanating from said extensive surface, the body being mounted on a printed circuit board, and the printed circuit board having channels therein for allowing fluid flow to cool said body.

According to a further aspect of the present invention there is provided an ultrasonic transceiver device for producing ultrasonic beams, comprising a body vibratable at ultrasonic frequencies and an extensive surface for beam emanation, the device configured to produce an unfocused power beam for thermal tissue damage, the unfocused power beam being produced by vibration over the body of the transceiver and emanating from said extensive surface, further comprising a pump for pumping fluid around said device to cool said device.

An embodiment may be attached to a catheter and said pump may be located within said catheter.

According to a further aspect of the present invention there is provided an ultrasonic transceiver device for producing ultrasonic beams, comprising a body vibratable at ultrasonic frequencies and an extensive surface for beam emanation, the device configured to produce an unfocused power beam for thermal tissue damage, the unfocused power beam being produced by vibration over the body of the transceiver and emanating from said extensive surface, the device being insertable into vessels where flow is present, and further comprising a flow directing structure for directing said flow present in the vessel over the vibratable body and/or the heat sink in order to cool said device.

In an embodiment, said flow-directing structure comprises a balloon.

In an embodiment, said flow directing structure comprises a shaft and a bending zone on the shaft, the bending zone directing said flow.

Unless otherwise defined, all technical and scientific terms used herein have the same meaning as commonly understood by one of ordinary skill in the art to which this invention belongs. The materials, methods, and examples provided herein are illustrative only and not intended to be limiting.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Implementation of the method and/or system of embodiments of the invention can involve performing or completing selected tasks manually, automatically, or a combination thereof. This refers in particular to tasks involving control of the ultrasonic system.

Moreover, according to actual instrumentation and equipment of embodiments of the method and/or system of the invention, selected tasks may be implemented by hardware, by software or by firmware or by a combination thereof using an operating system.

For example, hardware for performing selected tasks according to embodiments of the invention may be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified schematic diagram of a first embodiment of an ultrasound transceiver providing a power beam over a surface extent according to the present invention;

FIG. 2 is a simplified schematic diagram illustrating the chimney effect set up by the ultrasound beam shown in FIG. 1;

FIG. 3 is a simplified diagram showing variations of a PCB on which to mount the ultrasound transceiver, the PCB having channels in various configurations for improving fluid flow around the transceiver, according to embodiments of the present invention;

FIG. 4 is a simplified diagram illustrating an ultrasonic transceiver in a catheter centered in a vessel or cavity using a balloon, according to embodiments of the present invention;

FIG. 5 is a simplified diagram illustrating an ultrasonic transceiver in a catheter centered in a vessel or cavity using a coiled placing wire, according to embodiments of the present invention;

FIG. 6 is a simplified diagram illustrating an ultrasonic transceiver in a catheter centered in a vessel or cavity using a placing net, according to embodiments of the present invention;

FIG. 7 is a simplified diagram illustrating an ultrasonic transceiver located in a window in the circumferential wall of a catheter, according to embodiments of the present invention;

FIG. 8 is a simplified block diagram illustrating a catheter and the control and operating elements that together with the catheter form a thermal tissue damage or ablation system for use in embodiments of the present invention;

FIG. 9 is a simplified flow chart illustrating a duty cycle control loop for controlling the duty cycle based on measured temperature, according to embodiments of the present invention;

FIG. 10 is a simplified schematic diagram illustrating a flow control device for controlling blood flow around the transceiver, according to embodiments of the present invention;

FIG. 11 is a simplified graph showing correlation between increase of voltage and increase in temperature during operation of the power ultrasound beam according to embodiments of the present invention;

Figure 1:
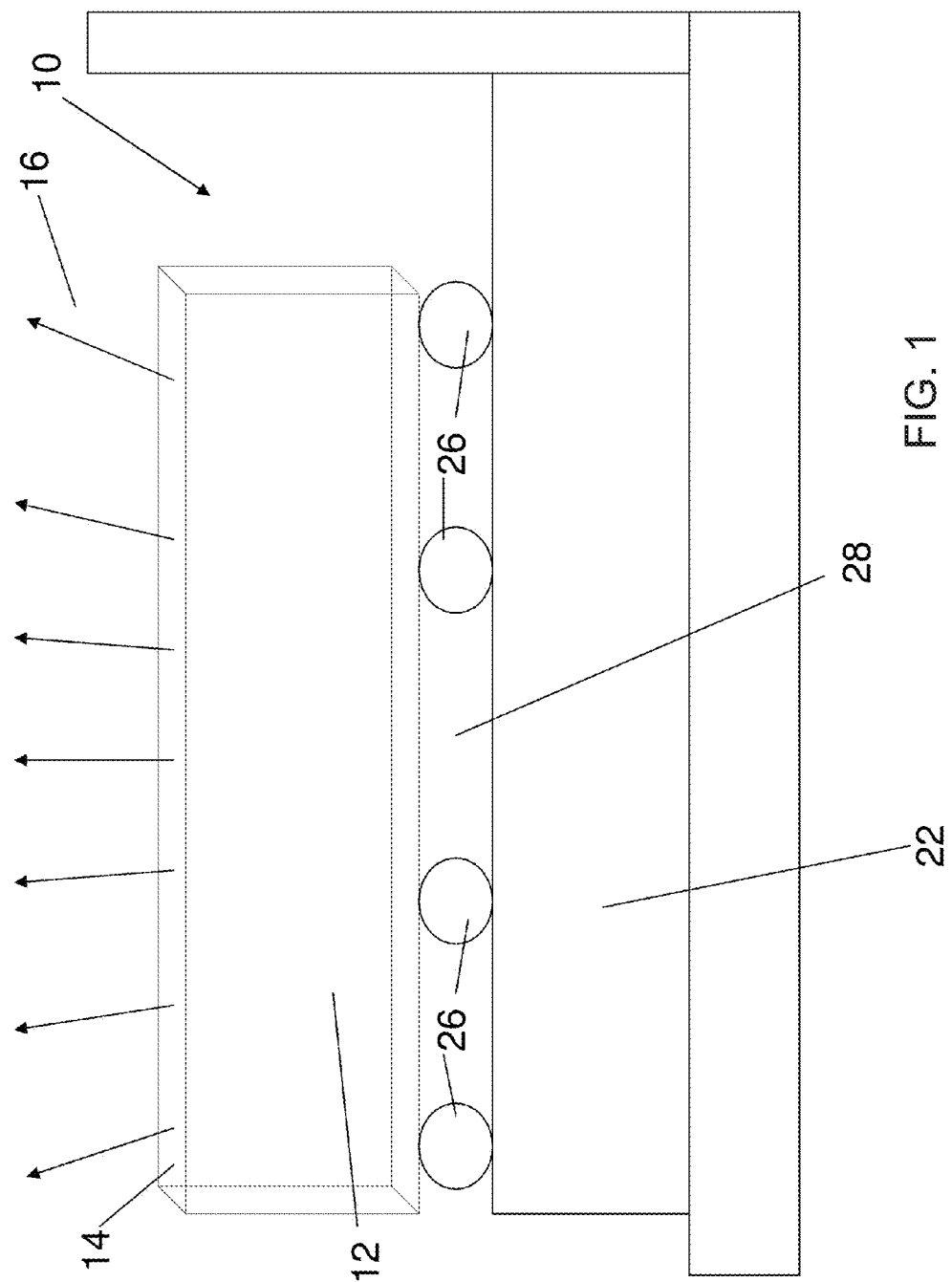
Figure 12:
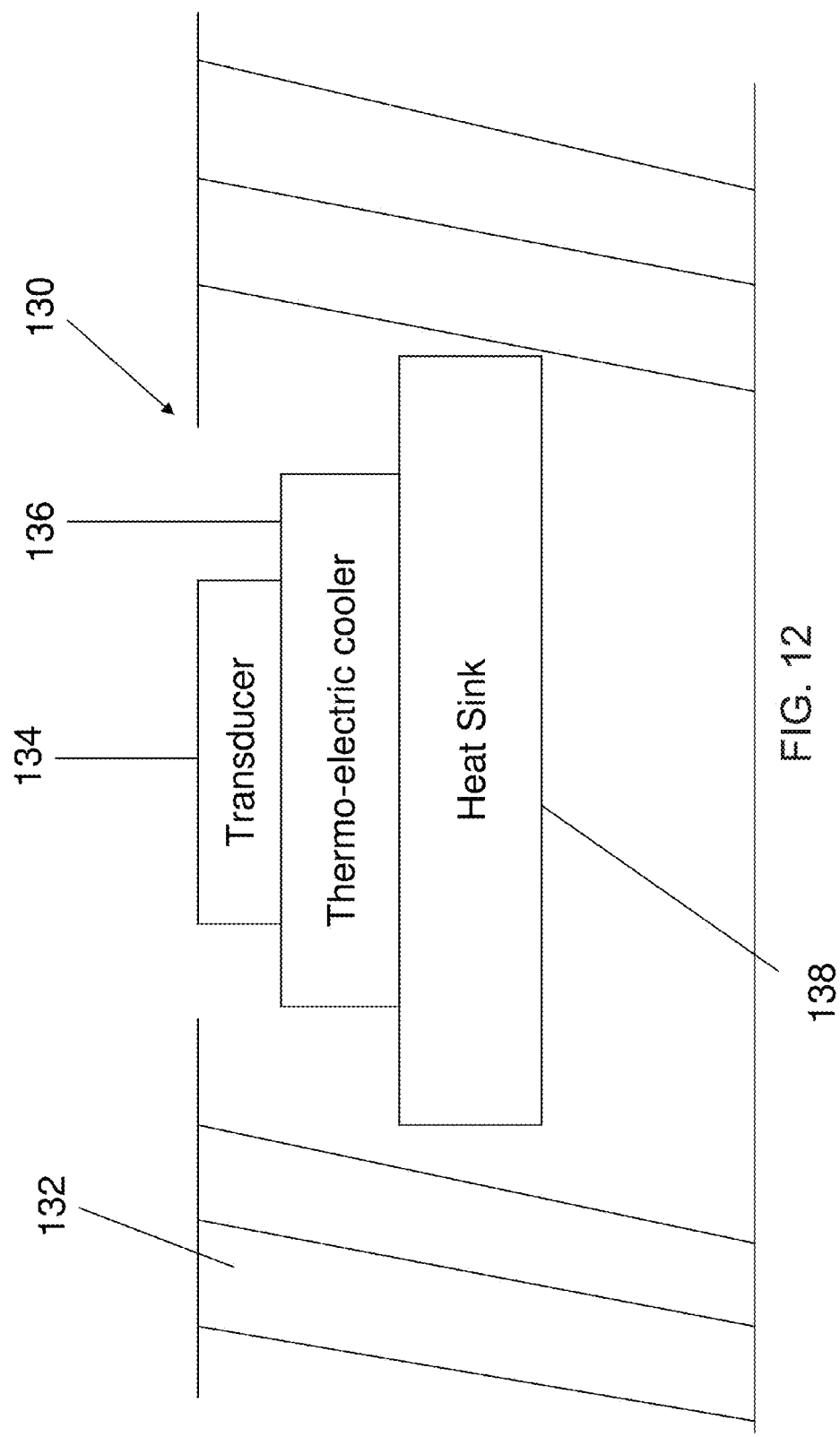
Figures 15A, 15B:
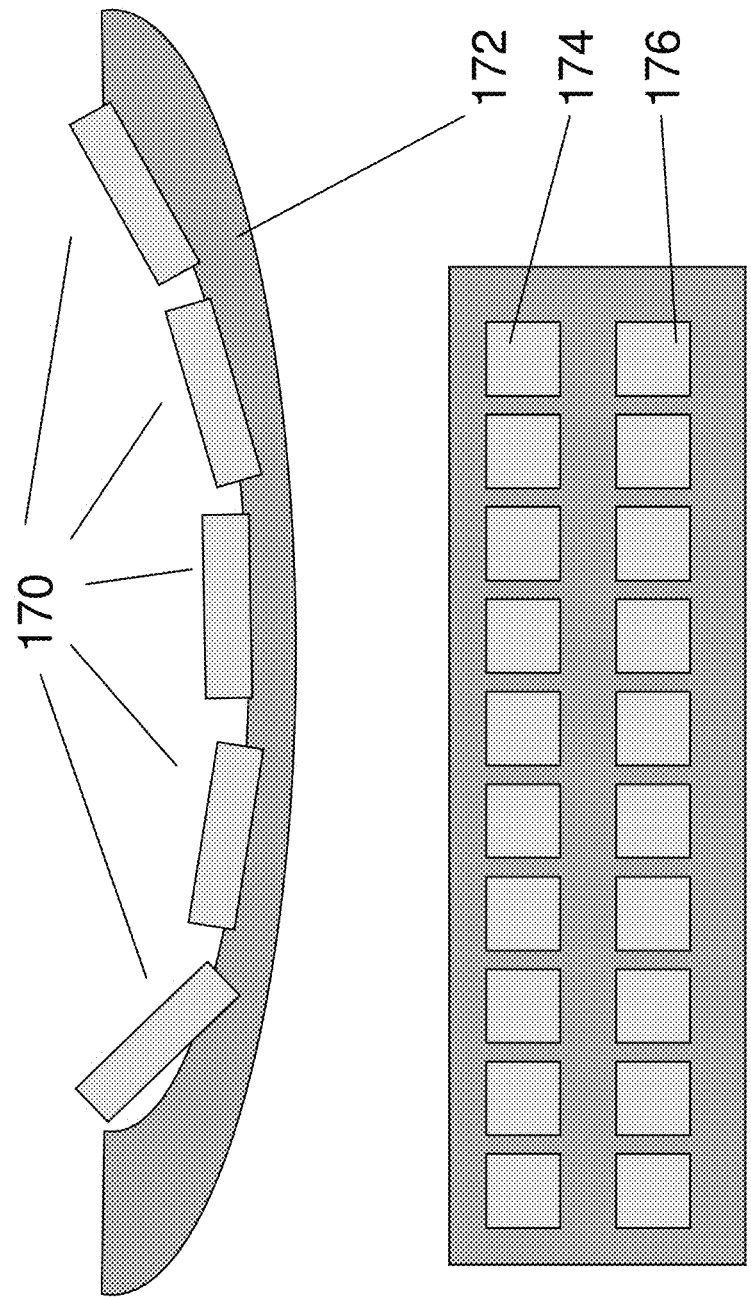
Figure 16:
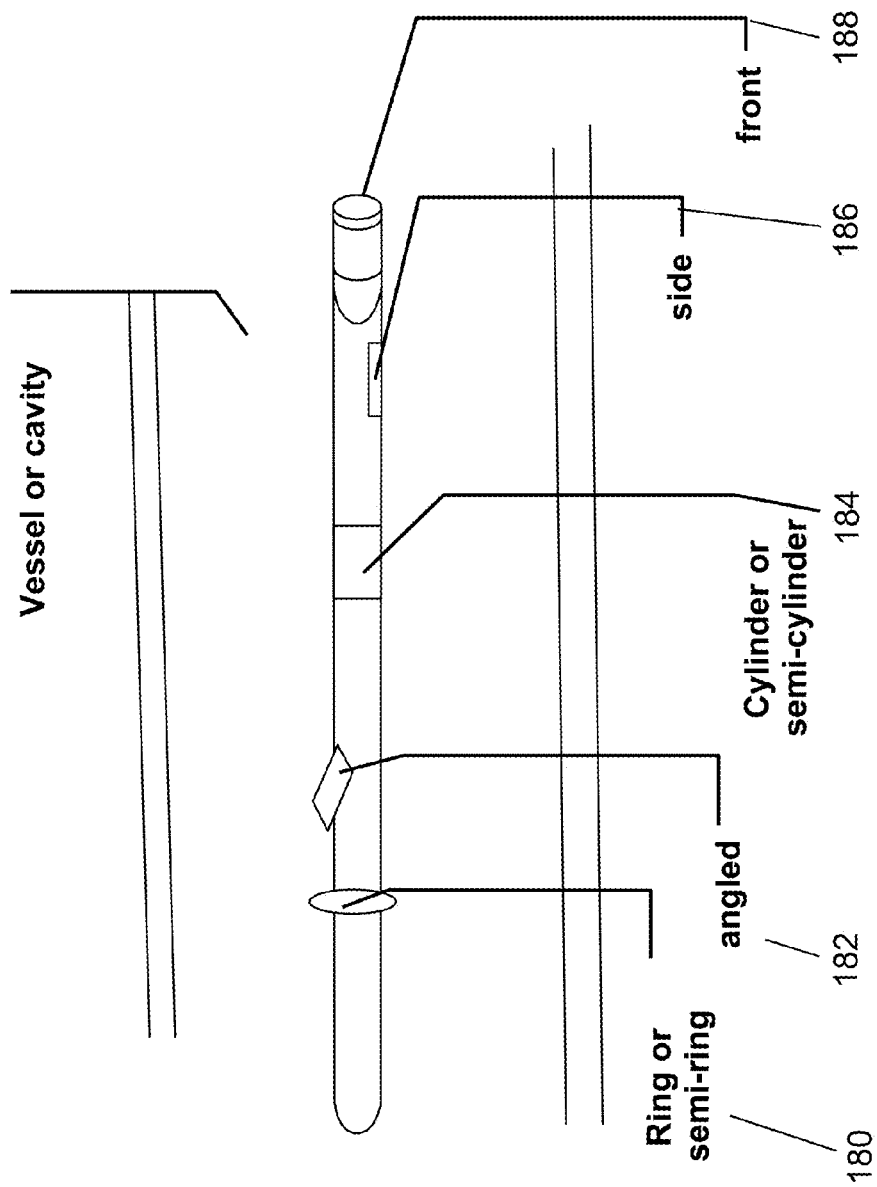
Figure 17:
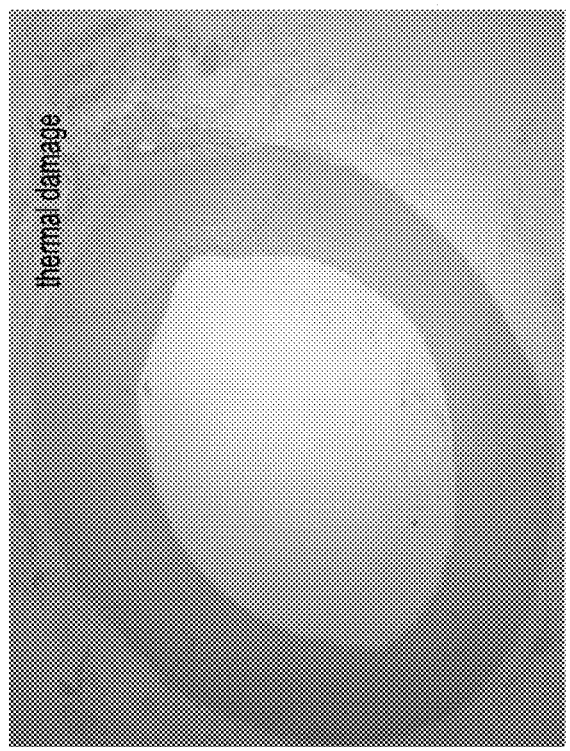
Figure 18:
Figure 19:
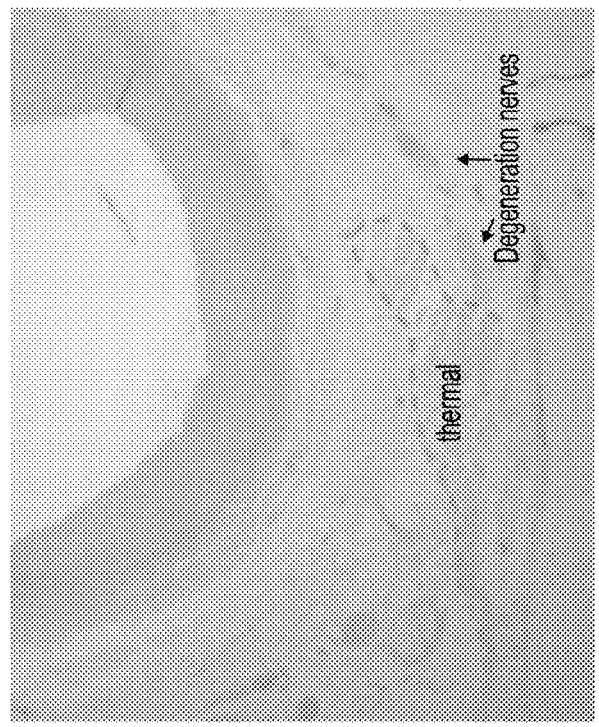
Figure 20:
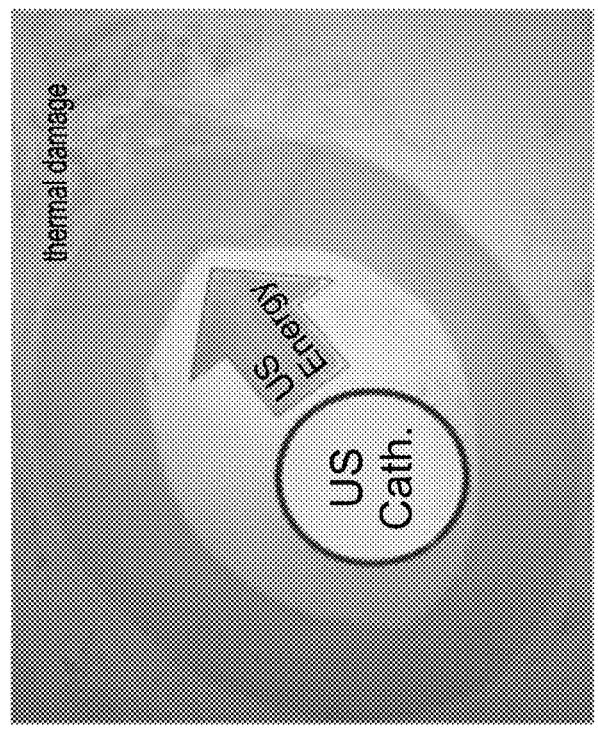
Figure 21:
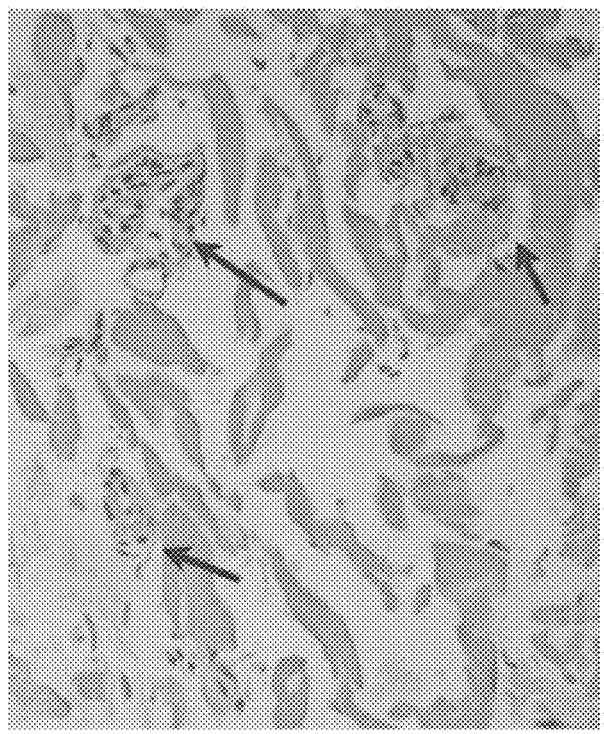
Figure 22:
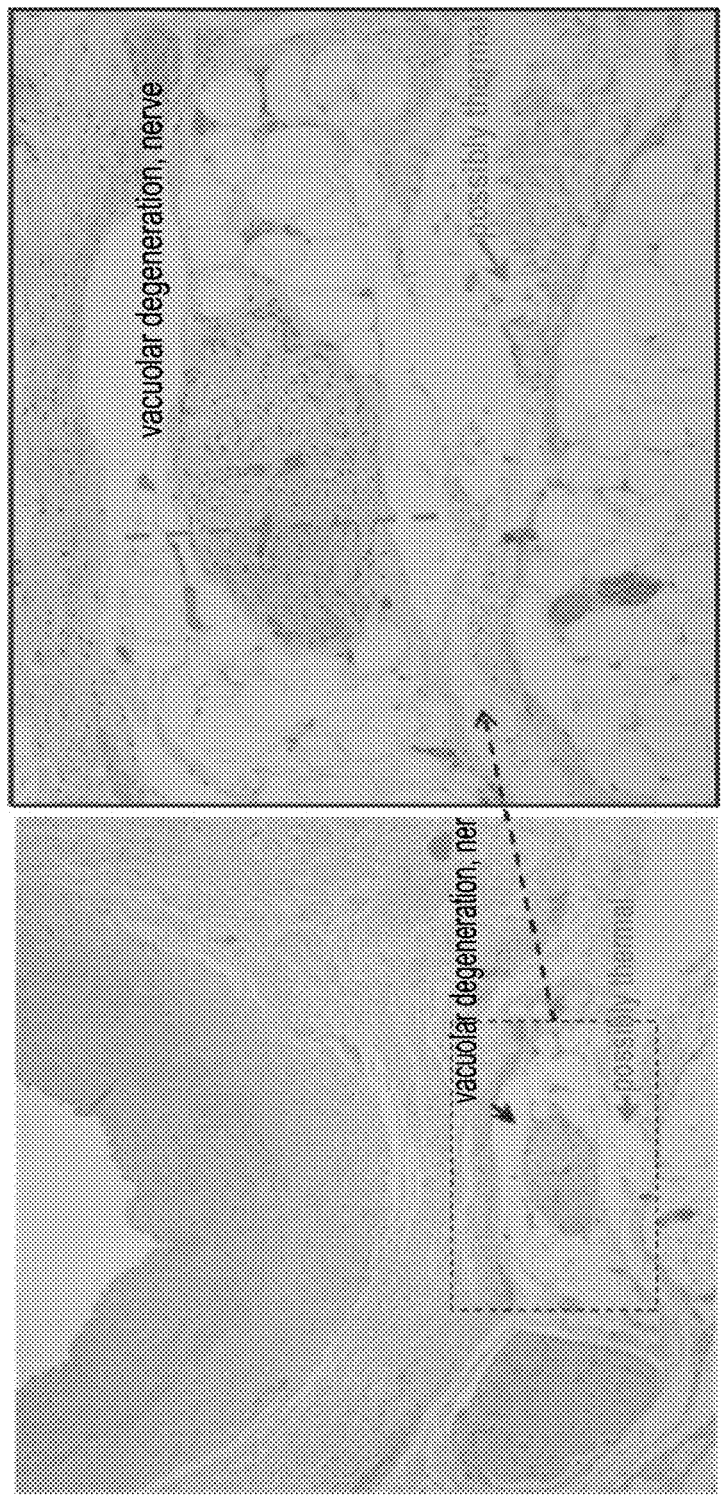

FIG. 12 is a simplified block diagram illustrating a variation of the device of FIG. 1 in which a thermo-electric cooler and a heat sink are used on a transceiver, the transceiver being mounted at a window of a catheter, according to embodiments of the present invention;

FIGS. 13A and 13B are simplified schematic diagrams illustrating variant rectangular and other shapes shown in cross section, of a piezoelectric element for the transceiver of FIG. 1;

FIG. 14 is a simplified diagram showing cylinder-based shapes shown in three dimensions of a piezoelectric element for the transceiver of FIG. 1;

FIG. 15A is a side view of a series of piezoelectric elements mounted on a single mounting according to an embodiment of the present invention;

FIG. 15B is a view from above of an arrangement of piezoelectric elements mounted in two rows according to embodiments of the present invention;

FIG. 16 is a simplified schematic diagram that illustrates a series of angles and positions in relation to a body vessel and a catheter, in which the transceiver can be placed by navigation;

FIG. 17 is a histology slide using H&E stain, and showing the thermal effect in a pig carotid artery;

FIG. 18 is a histology slide using H&E stain, and showing the thermal effect in a pig renal artery;

FIG. 19 is a histology slide wherein analysis and marking of the thermal damage area to a pig Carotid Artery is made by a trained pathologist;

FIG. 20 is a histology slide wherein analysis and marking of the thermal damage area to a pig Renal Artery is made by a trained pathologist;

FIG. 21 is a histology slide showing analysis and marking of the blocked Vasa-Vasorum, with arrows placed by a trained pathologist in a pig Carotid Artery Vasa-Vasorum in the adventitia; and FIG. 22 shows two histology slides with analysis and marking of the thermal damage, or nerve degeneration area, made by trained pathologist, for a pig renal artery, and nerves in adventitia.

DESCRIPTION OF THE PREFERRED EMBODIMENTS

The present embodiments comprise an ultrasound transceiver device and cooling thereof and, more particularly, but not exclusively to the cooling of such a transceiver device within a small vessel which may be filled with fluid.

The present embodiments may provide a transceiver which carries out thermal tissue damage using an ultrasound beam, for example an unfocussed beam produced over the body of the transceiver and emanating from an extensive surface of the transceiver, as opposed to prior art focused beams which are produced in tightly defined spots. The beam heats surrounding fluid opposite the extensive surface and sets up a chimney effect which provides convective cooling to the transceiver extensive surface.

The transceiver may be mounted on a PCB and trenches may be constructed in the PCB for fluid flow to enhance the cooling effect. In addition pumping methods may be used to enhance the flow of liquid around the transceiver.

An embodiment uses an airbacked transceiver in which surface tension is used to retain the air in position. Thus the transceiver does not need to be sealed. Connections to the PCB across the airgap may use heat conductive materials to ensure that the PCB is in thermal contact with the transceiver and thus enabling the PCB to act as an additional heat dissipation surface. A metal channel may be provided in the PCB.

The transceiver may be located on a catheter, either at a window in the side wall of the catheter or at the distal tip of the catheter. In such a case the transceiver may be thermally connected to a heat sink that is located wholly or partly within the catheter. The heat sink can, in some embodiments, evacuate the heat to the surroundings or to cooling liquids such as blood. In addition, saline may be pumped down the catheter to provide additional fluid flow around the transceiver and/or the heat sink, and the heat sink can be part of the shaft of the catheter as will be explained in greater detail below.

The transceiver may provide a power beam and a measuring beam and a method is provided for measuring increases in temperature and stopping operation or changing the duty cycle or/and applied power if overheating is detected.

The power beam may be provided at frequencies at or in excess of 20 Megahertz, and using piezoelectric transceivers which are below two millimeters in thickness, to avoid problems with cracking due to thermally induced stress within the transceiver.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1, which illustrates an ultrasonic transceiver device 10 for producing ultrasonic beams. Device 10 comprises a body 12 which is vibratable at ultrasonic frequencies by an input electrical signal, and a surface 14 which extends over the body, for beam emanation. The device may produce an unfocused power beam, indicated by arrows 16, for thermal tissue damage or like purposes that require relatively high power. The unfocused power beam is produced by vibration over the body 12 of the transceiver and emanates from over an extent of the surface. The beam heats fluid opposite the surface and because the heating effect occurs over the surface extent it sets up a chimney effect in the fluid. The extent of the surface thus becomes subject to convective cooling when immersed in a fluid and producing the power beam.

Figure 2:
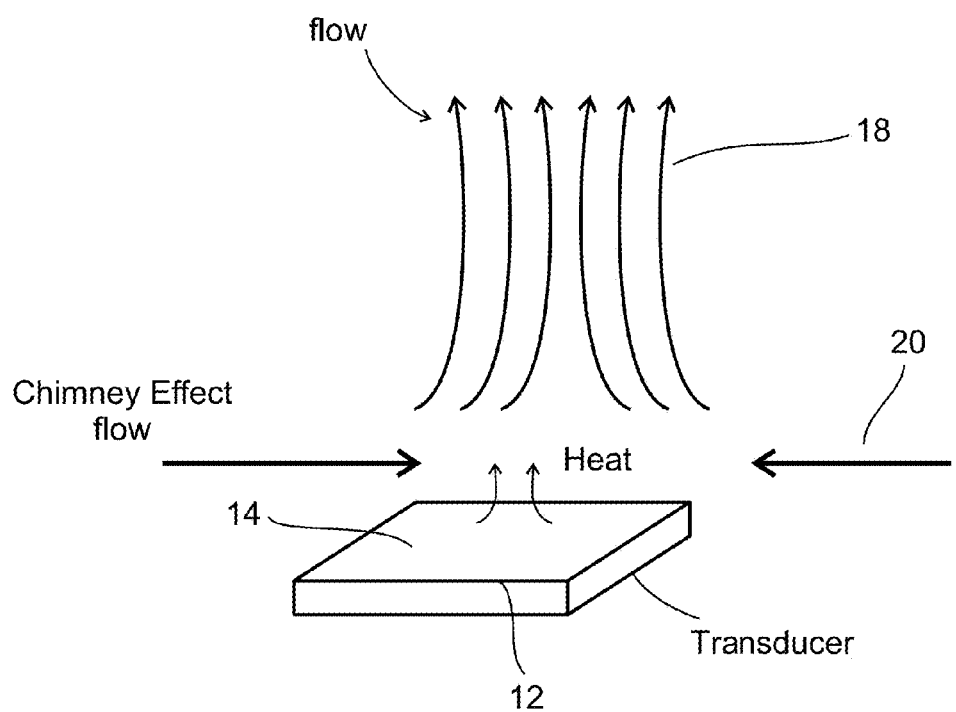

Reference is made to FIG. 2 which is a simplified schematic diagram illustrating the chimney effect. Liquid up against the hot surface 14 above the transceiver body 12 is heated by the beam and its density is reduced causing it to be displaced by lower density cooler fluid. The displacement is in the direction of arrows 18, typically in a direction normal to the surface 12 being heated as long as the heating effect is over a surface extent. If the heating is point heating then the chimney effect is not set up. Cooler liquid is thus sucked in from the sides as indicated by arrows 20.

Returning to FIG. 1, and the device may be mounted on a PCB 22. The ultrasonic transceiver device itself may be a piezoelectric element, which vibrates in response to electrical input and which produces an electrical output when itself vibrated.

Connection mountings 26 on the PCB are used to mount the transceiver. The connection mountings allow a gap 28 to be formed between the transceiver and the PCB. As will be explained in greater detail below, the PCB can be connected to a conductive heat pad or other heat dissipating mechanism.

The gap 28 may be air-filled, and may be sealed to retain the air when the device is immersed in liquid. However the sealing can attenuate the ultrasonic energy and thus, in an alternative embodiment the gap may be unsealed. In such an embodiment, surface tension may retain air within the gap when the device is immersed in fluid.

The conductive connections 26 to the PCB across the airgap 28 may provide thermal conductivity as well as electrical conductivity, thereby enabling the PCB 22 to act as an additional heat dissipation surface.

Figure 3:
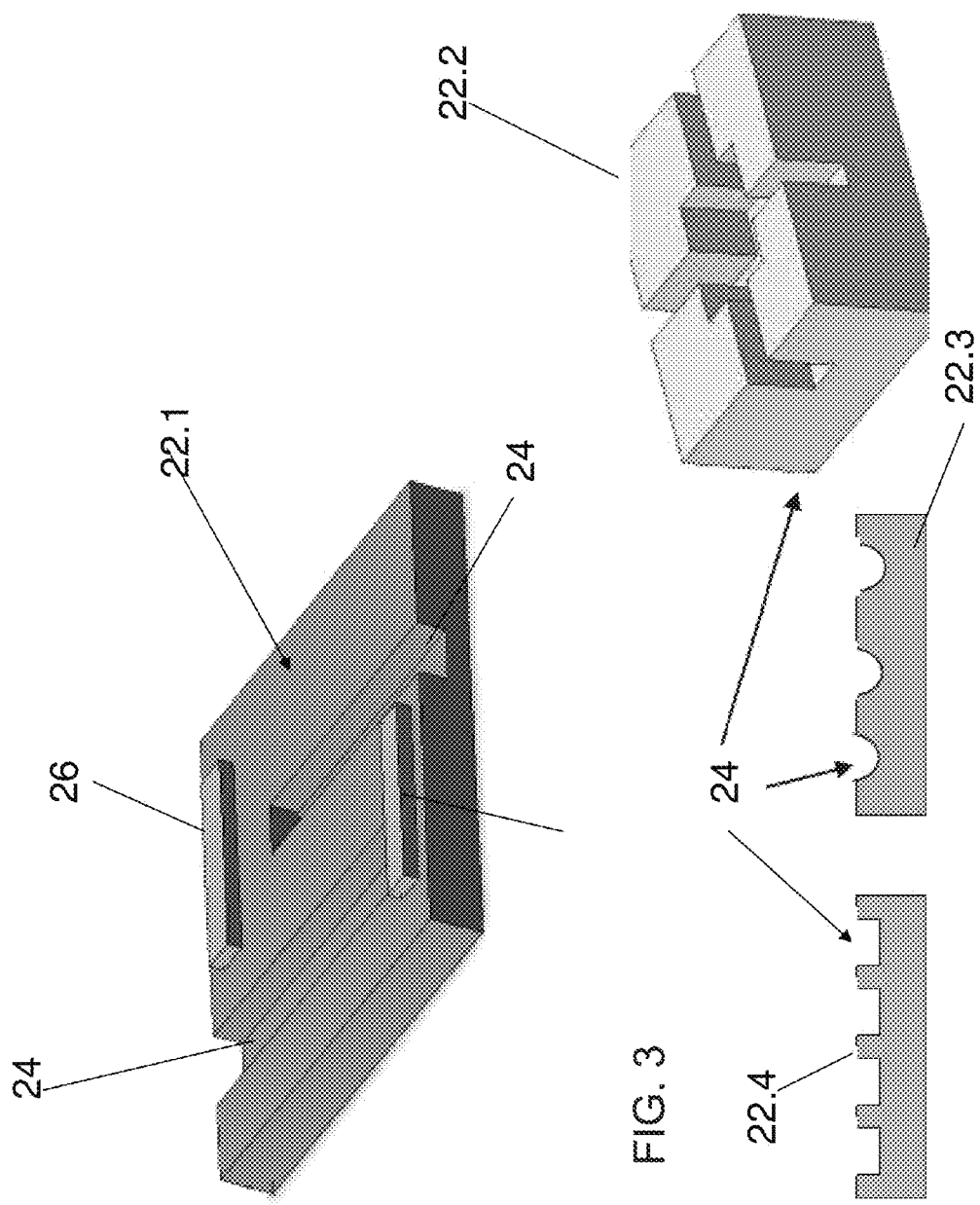

Reference is now made to FIG. 3, which shows four exemplary structures 22.1, 22.2, 22.3 and 22.4, for the PCB. As shown in FIG. 3, the PCBs 22.1 ... 22.4 include trenches 24. In the PCB 22.1, the transceiver is mounted between connection mountings 26, and the trenches 24 thus pass underneath the transceiver to allow fluid flow under the transceiver to assist with cooling.

In many cases the transceiver is operated in blood vessels such as arteries where there is significant fluid flow. However other body vessels may have little or no natural flow within them, in which case a pumping mechanism or pumping unit may be provided for actively pumping liquid around the transceiver. In some cases, even arteries may require some augmentation to the fluid flow via artificial pumping.

Figure 4:
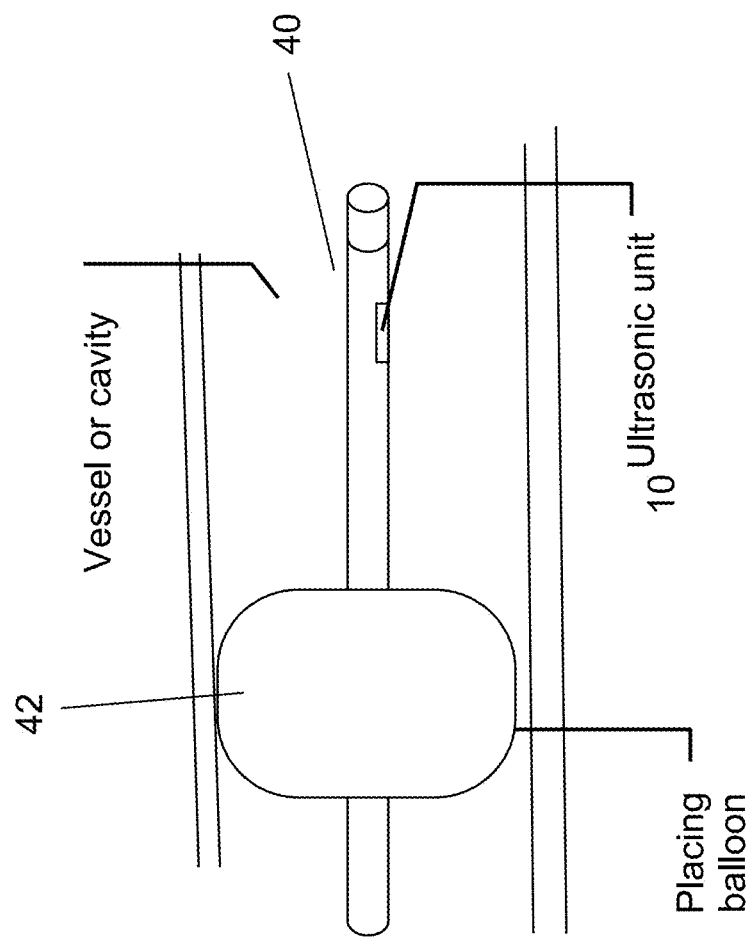
Figure 5:
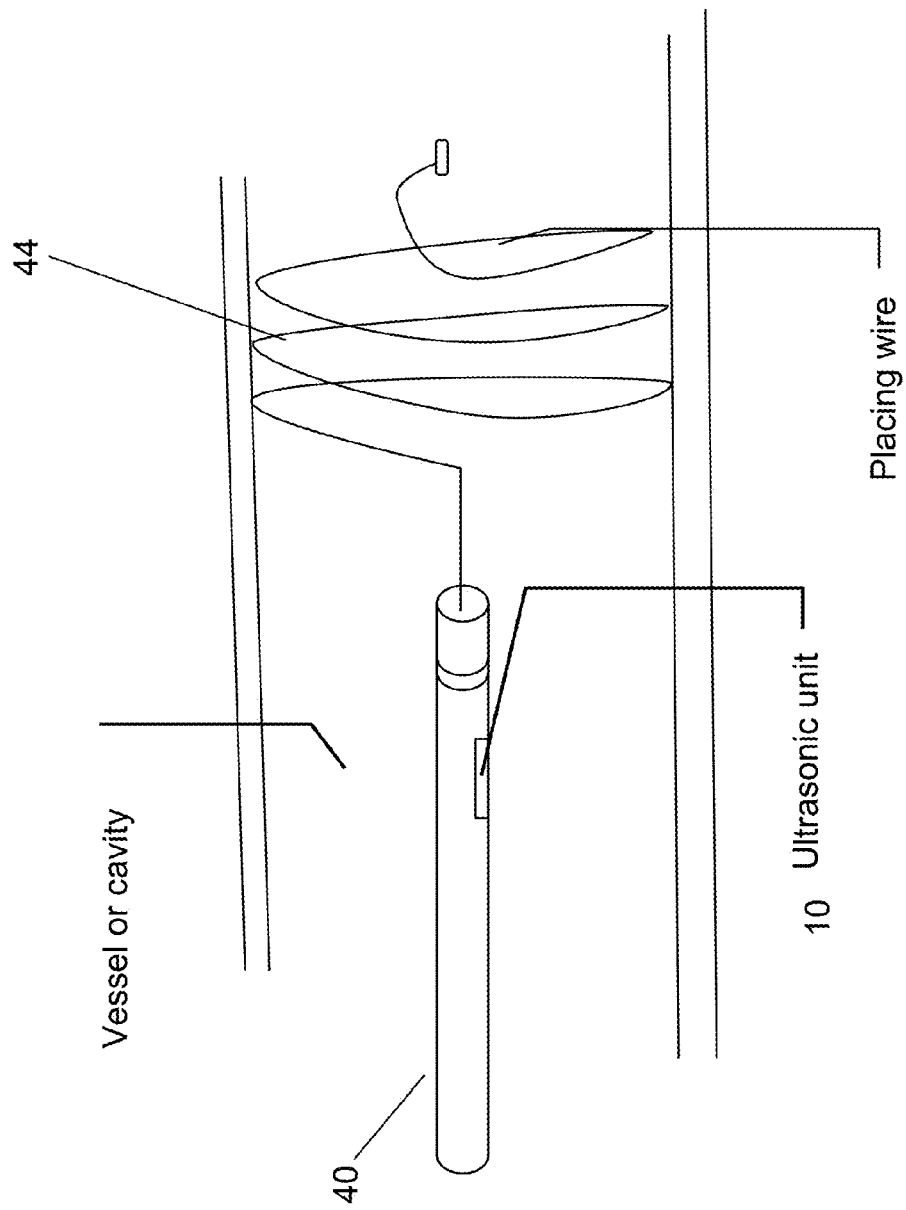
Figure 6:
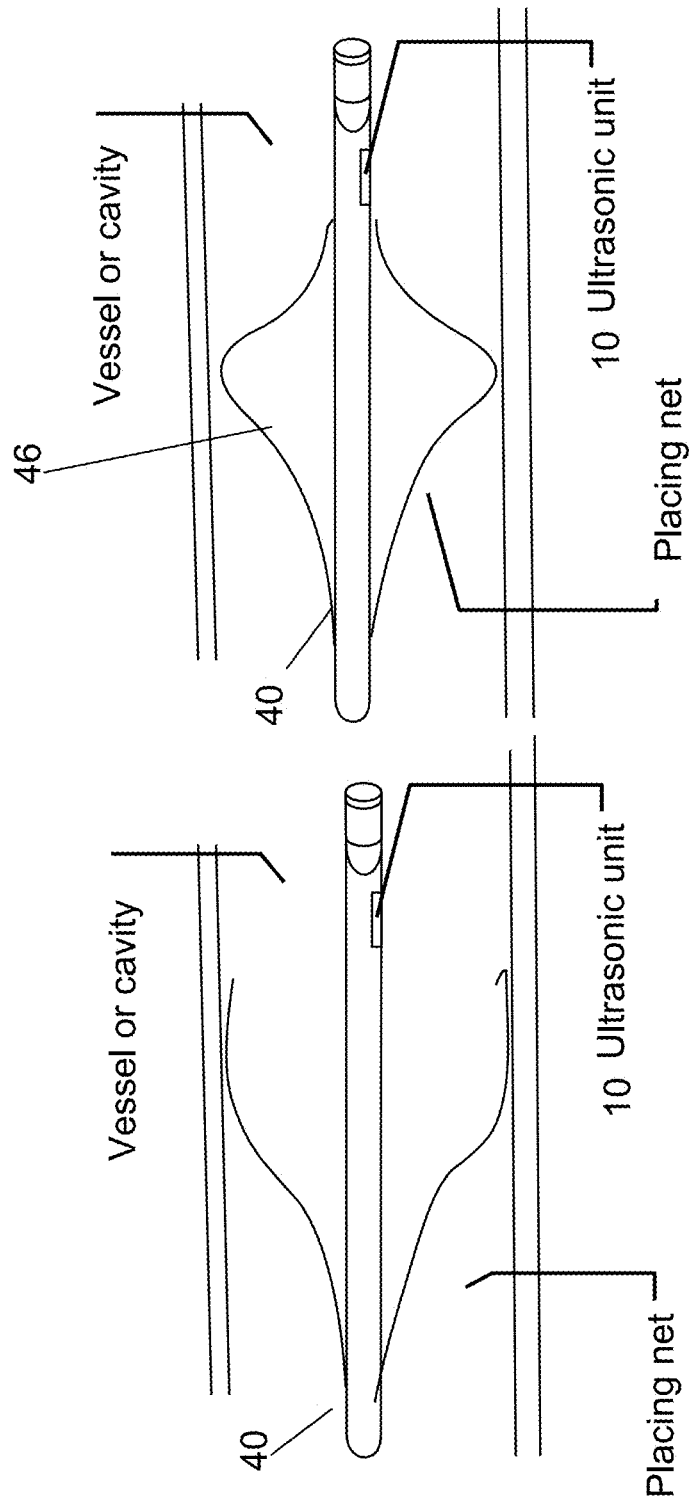

Referring generally to FIGS. 4, 5 and 6, the transceiver device 10 is typically inserted into a body vessel using a catheter 40, and in use is located at a window in the catheter, which window is in these cases on the circumferential wall close to the distal end of the catheter. Alternatively the device could be placed on the distal end itself of the catheter.

Pumping of saline down the catheter may provide the artificial pumping referred to above. The transceiver device may be thermally connected to a heat sink that is located within the catheter. Typically cooling fins cannot be used in blood flow due to the danger of breaking platelets and causing thrombus, or blood clots. Thus the heat sink may be retained wholly within the catheter. Saline may be pumped down the catheter to provide fluid flow around the transceiver and around the heatsink.

Braiding may be provided in the catheter, say using copper stripes or stainless steel braiding, to use the entire length of the catheter as a heat sink surface.

In FIG. 4, the catheter is held in place in the middle of the vessel away from the wall by a balloon 42. In FIG. 5 a spring 44 keeps the catheter centered with respect to the wall. The spring may be made of Nitinol, a shape memory alloy which can be inserted flat and then when attaining a pre-set temperature reassumes its remembered shape. In FIG. 6 a placing net 46 is used to position the catheter with respect to the wall.

Distancing the transceiver from the vessel wall ensures that the transceiver does not directly heat the vessel wall. Furthermore the distance allows for fluid flow around the transceiver and thus allows the chimney effect to occur. Furthermore the distance allows for blood flow at the wall of the vessel thus allowing the epithelium cells at the wall of the blood vessel to be cooled by the flow of blood and thus not be damaged by the heating effect of the ultrasound beam. Damaged epithelium cells are a future risk for the blood vessel. In general the thermal damage effect that the ultrasound beam uses is the denaturation of collagen, which occurs at around 55° C. The blood flow is generally sufficient to ensure that the epithelium layer does not reach this temperature.

Figure 7:
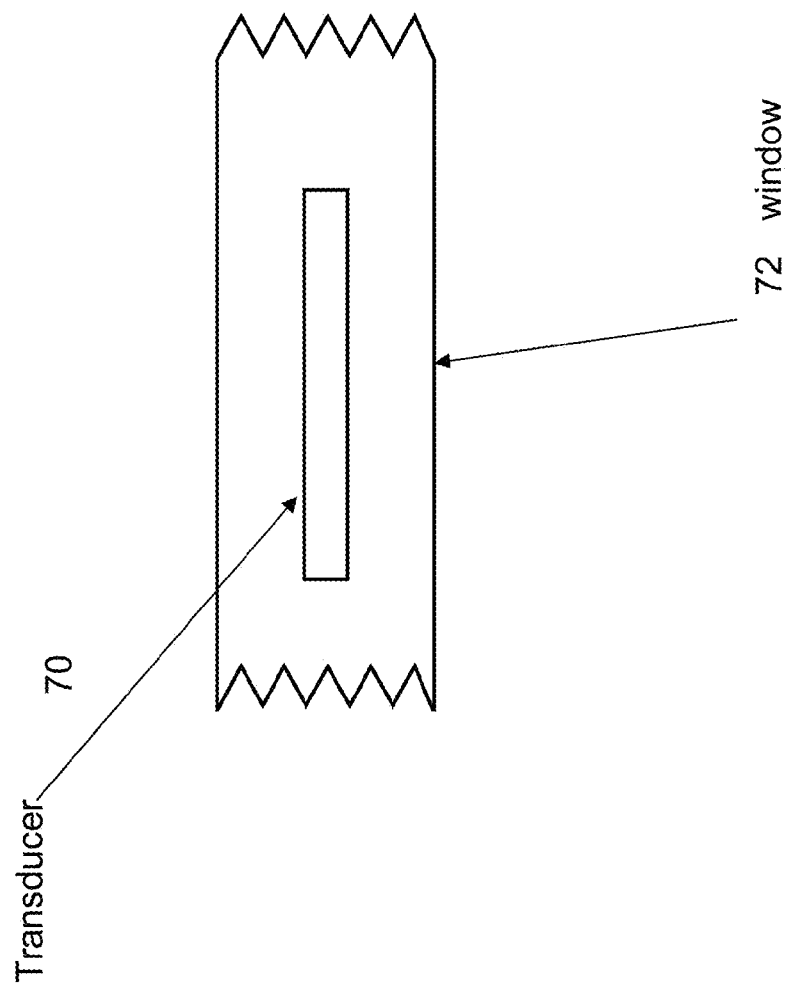

Reference is now made to FIG. 7, which shows a transceiver 70 mounted in a window 72 of a catheter. The chimney effect around the transceiver can have the additional effect of sucking in injected medication or staining substances from the catheter through the window 72, thus improving injection efficiency.

A temperature sensor may be provided with the transceiver. Typically, the sensor is placed just downstream of the transceiver in the blood flow direction. Thus the temperature that is measured is that of liquid that has just passed the transceiver surface, and increasing measured temperature may be taken as an indicator of overheating in the transceiver.

Figure 8:
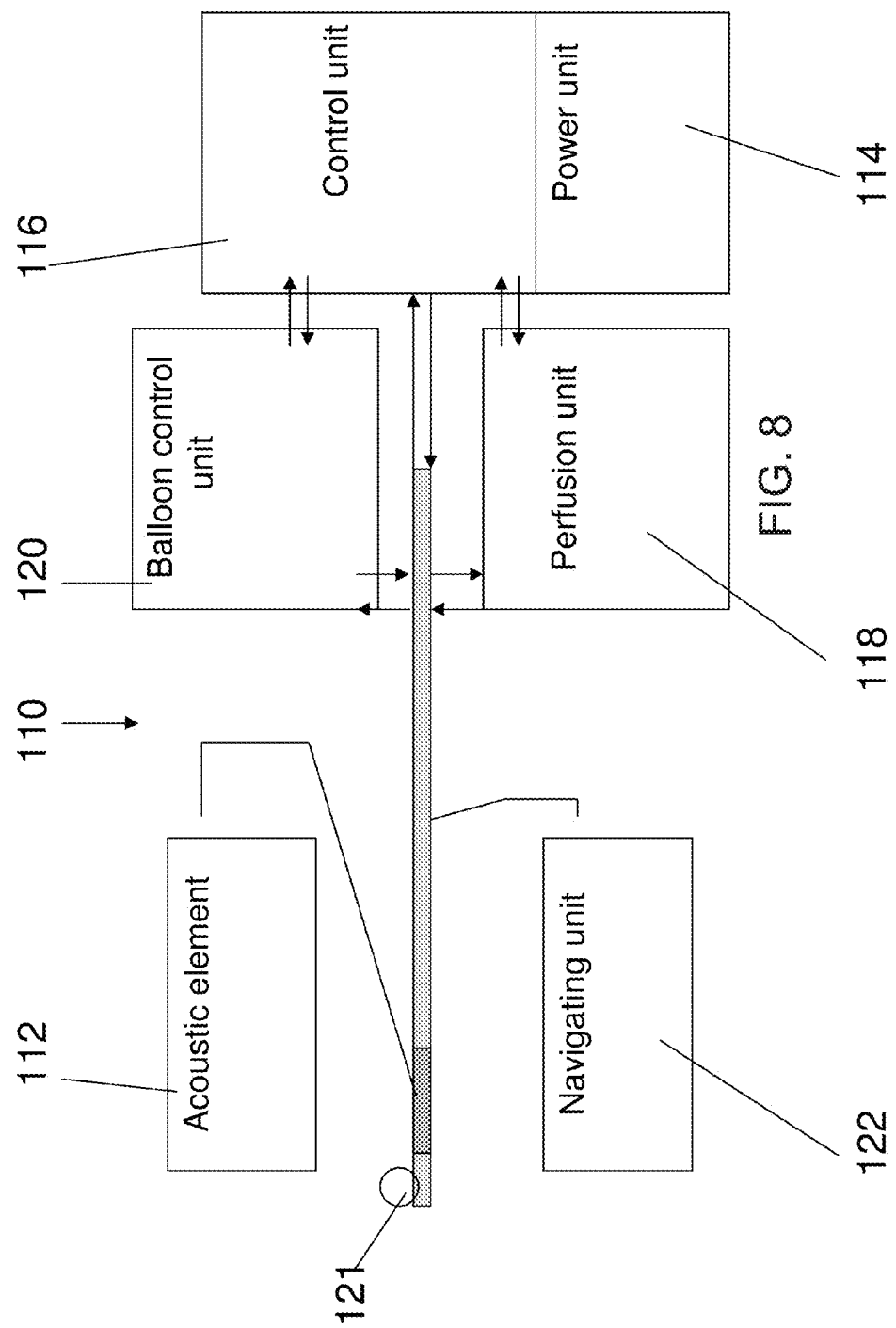

Reference is now made to FIG. 8, which is a simplified block diagram of a system according to an embodiment of the present invention. In FIG. 8, the system 110 may contain an acoustic transceiver 112, a power supply unit 114, a control unit 116, a pumping or circulation unit, shown as perfusion unit 118, a balloon control unit 120, temperature sensor 121, and a navigating shaft 122.

The navigating unit allows the acoustic element to navigate to the location or locations at which it is needed. The balloon control unit controls a balloon for supporting the lumen as needed and centering the catheter as discussed. The perfusion unit provides injection substances as necessary.

Figure 9:
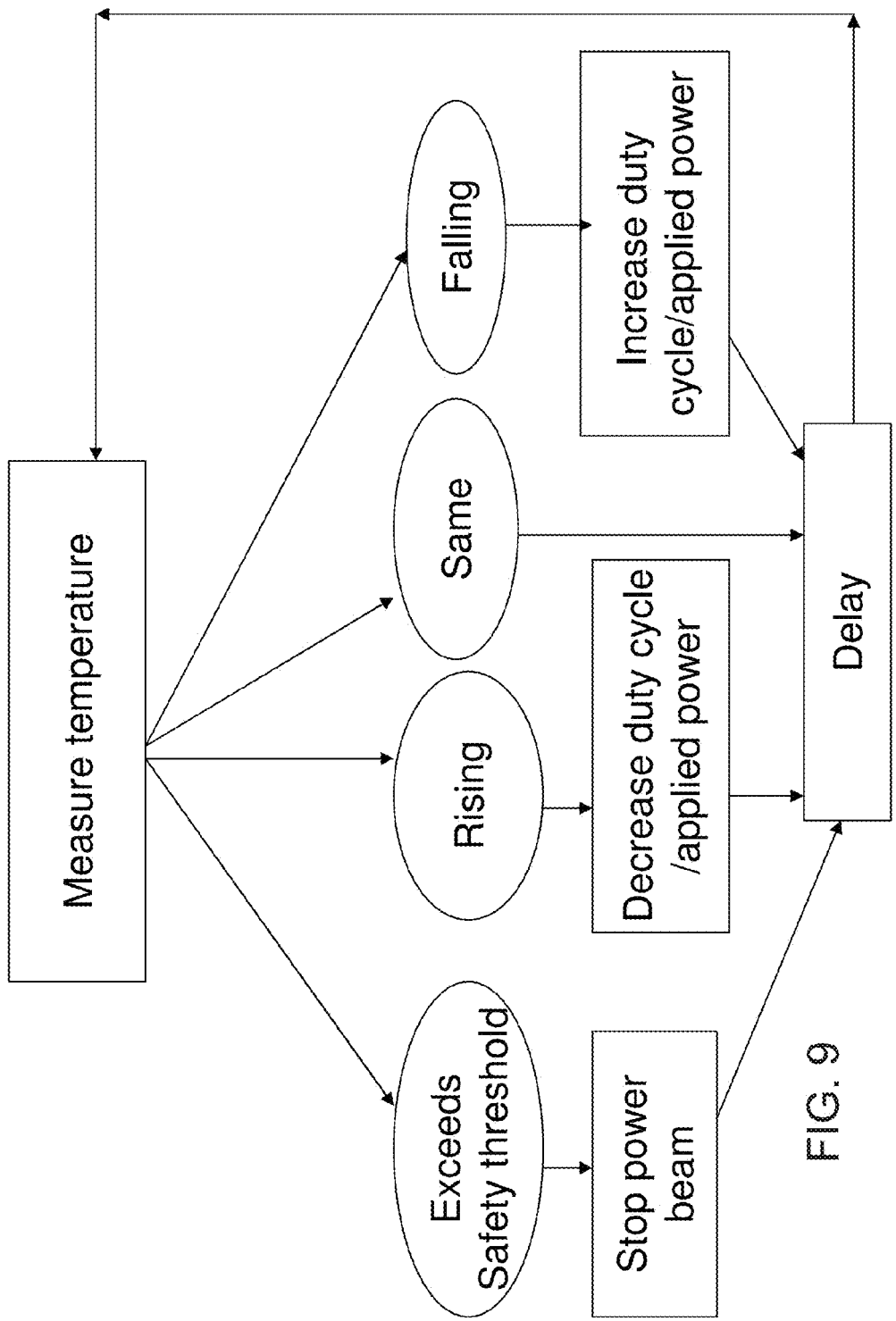

Reference is now made to FIG. 9 which is a simplified flow chart to illustrate how the controller 116 may vary the duty cycle of the power ultrasound beam in accordance with the temperature measured at temperature sensor 121. Controller 116 may provide the power beam in a duty cycle and/or just by controlling a level of applied power. The duty cycle and/or applied power may be increased if the temperature falls, kept the same if the temperature remains constant and decreased if the temperature rises. The duty cycle and/or applied power may for example be controlled to keep transceiver surface 14 within a range of 40° C. to 50° C., or at 44° C., or at other temperatures as deemed appropriate.

The controller 116 may stop the power beam when the temperature sensed by sensor 121 reaches or exceeds a predetermined safety threshold.

As explained above, in one embodiment the transceiver is located in a window or at the end of a catheter, and the temperature sensor is used to control a rate at which cooling saline is pumped down the catheter to provide fluid flow around the transceiver.

Figure 10:
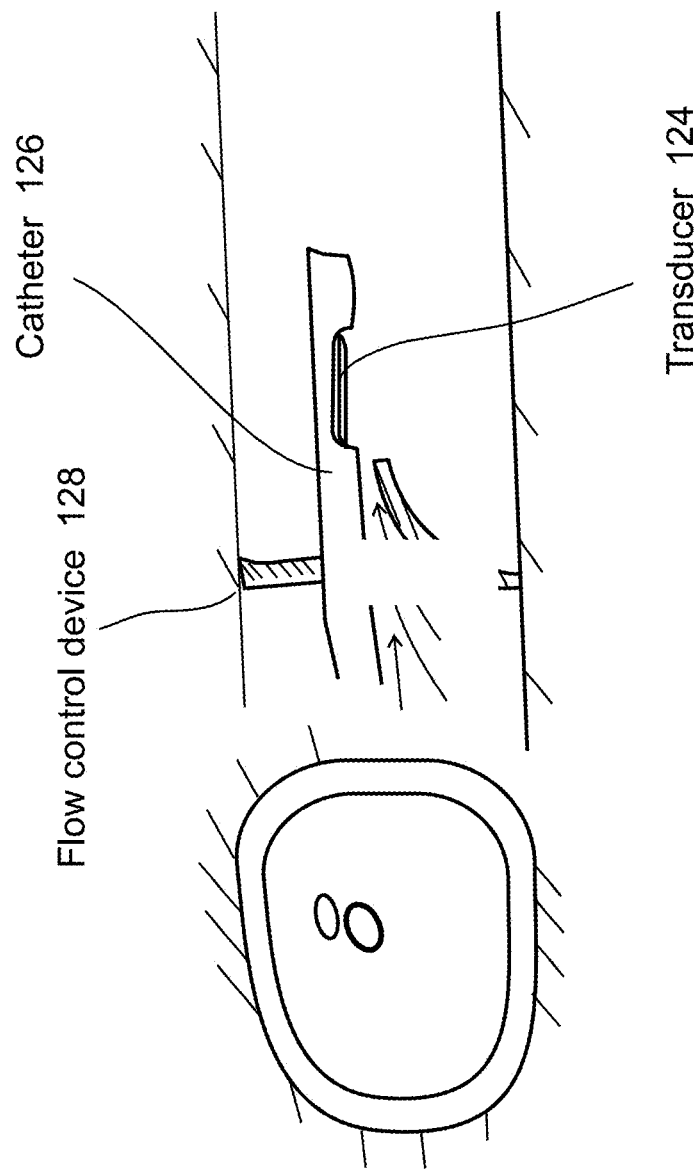

As well as controlling the pumping of saline from the catheter, it is also possible to control the blood flow rate within the vessel, for example using a balloon valve. Reference is now made to FIG. 10 in which a transceiver 124 is mounted at a window of catheter 126. A valve flow control device 128 sits around the catheter and can be opened or closed to change the blood flow around the transceiver.

As well as saline, contrast agents or medicines may be injected via the catheter and these too may provide an auxiliary role of helping to cool the transceiver.

Figure 11:
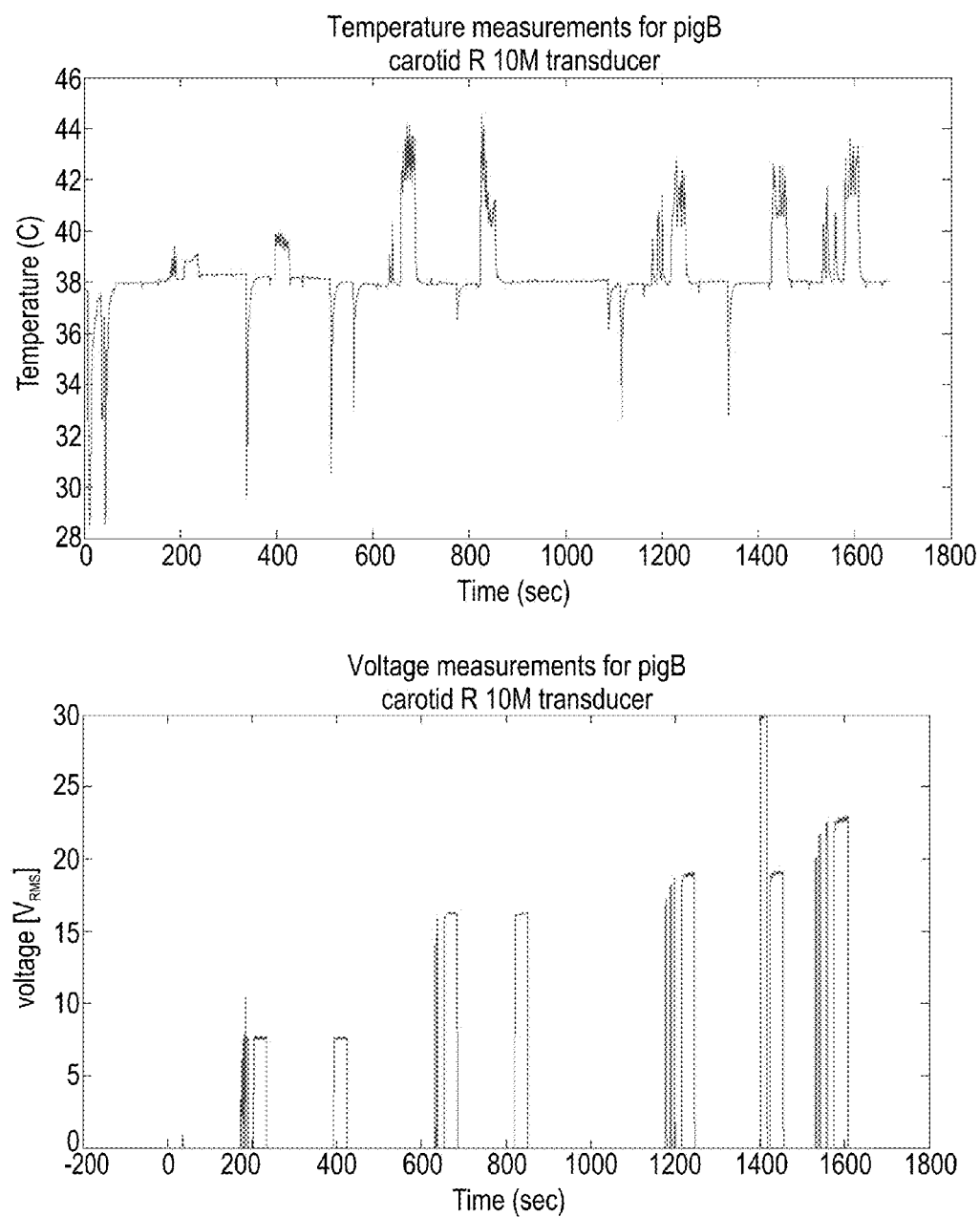

Reference is now made to FIG. 11, which shows temperature measurements in the upper graph against voltage in the lower graph for a transceiver according to the present embodiments. Specifically, FIG. 11 shows a graph of real time measurements of voltage and temperature in the renal area. The relation between the applied voltage and the temperature can easily be observed.

In addition in the temperature graph falls in temperature for example at t=350 [sec]; 600 [sec]; 1150 [sec] are seen. These drops are due to cold (25[° C.]) saline injection. Use of cold saline is an additional method of cooling that may be used.

Heat in the transceiver is directly proportional to voltage. In addition the heat is directly proportional to the reciprocal of impedance and to the efficiency subtracted from unity. Heat is additionally proportional to the liquid flow over the transceiver surface. The above may be expressed algebraically as:

$$\text{heat} \uparrow \alpha V \uparrow / Z * (1-\text{eff}) \text{ and heat} \uparrow \alpha \text{flow} \uparrow.$$

The blood flow rate may be calibrated with the heating and cooling effects. Thus it may be possible to turn on the transceiver, check the temperature, check the flow rate, and then use a calibration table to provide the correct cooling.

Reference is now made to FIG. 12, which is a simplified diagram illustrating an embodiment of the present transceiver device in which additional cooling elements are provided. Located at window 130 of catheter 132, a transceiver 134 is connected to a thermoelectric or peltier cooler 136 which in turn is connected to a heat sink 138. Typical dimensions for the construction are 0.8 mm overall, wherein 0.5 mm is the thickness of the heat sink. Alternatively, the TEC and\or the heat sink may be placed in the axial direction of the catheter or as part of the catheter shaft. It is noted that if attempting to use high power ultrasound over the entire body of a piezoelectric element, there is a problem with breakage of the transceiver due to thermal differences within the element. Ceramics generally have low thermal conductivity.

The present embodiments avoid the above problem by using relatively high frequencies, in the range of 8 or 10 to 40 MHz, which permits the use of thinner ceramics, so that the issue of thermal differences does not arise, or at least does not lead to breakage of the elements. Specifically, a frequency range of 10-40 MHz provides heating effects over a range of millimeters, and has been used for imaging but not at high power for tissue damage. The thinner ceramics are less than 0.25 mm in thickness and an example uses 0.15 mm.

As mentioned with reference to FIG. 9, control may be achieved by managing either the duty cycle or the applied power.

To date, imaging has used unfocused beams but at low power, whereas thermal tissue damage has used high power beams which have always been at lower frequencies and focused. Imaging uses short pulses followed by gaps to listen to the echo. Thermal tissue damage uses continuous or long bursts in a duty cycle. Imaging to follow the results may be carried out during the gaps in the duty cycle.

As mentioned above, the duty cycle can be changed as part of a control loop to maintain the correct temperature at the transceiver surface.

Imaging can be used to obtain the face of the vessel or lumen wall and thus to provide a further control loop to make sure that the transceiver is kept away from the wall.

The present embodiments are now considered in greater detail. The present embodiments relate generally to devices, parameters and methods for the treatment of tissue using ultrasonic waves in particular for heating, at a target area such as in the wall of a tube or cavity, located in the living body. The treatment may involve excitation using high power acoustic energy.

The ultrasonic effect is achieved in such a way that there is control over the heated target tissue volume and location. Preferably, a controlled volume of tissue between the ultrasonic element and the target tissue, is not treated. This distal effect may be achieved without the need of mechanical contact with the cavity walls.

Detailed application of the above includes the ability to cause moderate thermal damage within a controlled volume at the outer side of a cavity wall without damaging the inner side of the vessel, the inner side including different types of epithelium.

The treatment method may be applied by creating a gradient of different temperatures in the tissue by the combined effects of: heating the tissue with high power ultrasound and cooling of the tissue using conduction and convection. The convection could be of natural fluid, for example blood flow, or by artificial injection of cooling liquid, for example cold saline injection. Additional temperature effects that are widely elaborated in other sources may also simultaneously influence the temperature gradient, for example—blood flow or capillary blood perfusion.

The heating control is performed by controlling the parameters of the ultrasonic field and the transmission protocol, including: transmission frequency, power, duty cycle and duration, as will be described in greater detail herein.

The treatment is controlled by feedback from the tissue using an echo received from the tissue during the treatment. Specifically, at high temperatures above 55° C. an irreversible change is created in the collagen fibers in the tissue; this change may be monitored using the ultrasonic echo from the tissue, which allows mapping of the damaged tissue area.

It is also possible to increase or\and to add effects by ejection of fluids into the treated area or at an upstream area in such a way that the ejected fluid is inserted into the vessel, typically through the vasa-vasorum or the adventitia lymph capillary.

Nevertheless, it is possible to control the flow in the vessel at different locations using different devices, for example a balloon opening in the vessel and again changing the treated effects in the tissue.

Typically, the ultrasonic transmission is applied at high power, high frequency and for more than one second. Heating of the tissue in the ultrasonic field is performed by absorption of the acoustic energy in a process of dissipation of mechanical energy. The absorption and influence of the energy on the tissue includes inter alia the following effects: a heating effect, a mechanical effect, a pressure effect, a sub-pressure and a cavitation effect.

Simultaneously with the transmission the cooling effect is achieved by liquid flow in the vessel or fluid present (for example blood, urine, lymphatic liquid, bile) or liquid active ejection.

The present embodiments may provide the possibility of transmitting the energy to a second side of a wall without touching the wall, for example a cavity or lumen wall. By not touching it is possible to increase protection for both the elements and the non target tissue by allowing fluid to flow on the cavity walls and on the transceiver surface. The liquid provides for cooling. The present embodiments may also allow for easier operation by not restricting the transceiver location.

The present embodiments may transmit a non-focused acoustic field to reach the target tissue. An advantage of not having to focus the field is that there is no need to control the tissue distance from the transceiver. For example renal denervation may be carried out simply by allowing the catheter to transmit a wide, high power acoustic field from a nonspecific location in the artery to a distal nonspecific location of the renal nerve.

Alternative embodiments may provide a focused beam at higher power.

Embodiments of the invention may allow ejection of materials into the treated area or to an upstream area therefrom in a way that the materials are inserted into the vessel, say through the vasa-vasorum or the adventitia lymph capillary.

The embodiments described herein allow sampling of the voltage created on the ultrasonic element due to echoes from the tissue and processing the data in such a way that the treated tissue is monitored.

Echo sampling and recording and or processing for measurement and monitoring can be performed simultaneously with the treatment. Such simultaneous treatment and analysis can increase the level of control of the treatment in real time and help ensure achievement of the desired results.

More specifically, the following information may be monitored from the echoes received within a vessel:
wall distance from the transceiver,
vessel layer (media, adventitia, peri-adventitia) position,
thermal effect in the tissue location and
area of the thermal effect.

The data analysis method may include echo intensity, backscatter, spectral signature mapping, elastography, classification according to classification matrix of tissues, and the ultrasonic effect.

The control unit may use the above data and analysis for increasing the treatment, or reducing the treatment, or stopping the treatment, or providing indications regarding the treatment stage, or providing indications to stop or to continue the treatment.

A therapeutic catheter with an ultrasonic transceiver may allow for transmission to the vessel from the inner side.

An ultrasonic transceiver may be placed in proximity to a wall, with an internal catheter and transmission to the outer side of the wall. In the case of limbs one transceiver can be placed externally on the outside of the skin and another in a blood vessel.

An endoscope system may include an ultrasonic element in its tip. The endoscope may be inserted through the skin and ultrasonic transmission may be provided to the outer side of the cavity.

The fluid control methods may include one or more of the following implementations:

A restrictor around the transceiver. The implementation may involve: placing the transceiver at a different location in the vessel, and controlling the flow;

A restrictor near the transceiver. The implementation may again involve placing the transceiver at a different location in the vessel, and controlling the flow;

A restrictor in front of (upstream of) the transceiver. The method may involve blocking the flow upstream in order to load the vasa-vasorum with liquid and particles.

A restrictor past, that is downstream of, the transceiver. The method may involve blocking the flow downstream of the transceiver to allow drug delivery specifically to the treated area;

The restrictor may be one or more of the following: a balloon, a wire, nets, or a thin plastic sheet.

Manipulation of in the tissue reaction to the ultrasonic treatment is possible by:

Injecting vasoconstriction materials into the blood, and in this way reducing the perfusion and heat evacuation from the tissue, or injecting or evoking micro-bubbles and increasing the heating by increasing absorption of the ultrasonic energy, or the evoked micro-bubbles may be produced by use of an additional separate transceiver.

Micro-bubble transportation through the cell membrane may be increased using the acoustic treatment, and may achieve a multiplied effect.

The tissue may be cooled before treatment in order to protect and or control the treated area and non-treated area.

Artificial opening of a minimal cavity surgery opening in the skin for insertion of the therapeutic catheter may be provided.

The ultrasonic field and/or the level of perfusion can be controlled and manipulated by influencing the body system in general.

Possible target tissues for the device include one or more of the following and their nearby tissues to douse cavities: arteries, veins, lymph vessels, intestine, esophagus, CNS, urine lumen, gall bladder lumen, Stomach, and Tear Trough.

Applications for the above-described embodiments include the following:

Blood vessel wall pathology. For example for an atherosclerotic lesion;

Healthy blood vessel wall treatment;

Treatment of tissue near the blood vessel wall, for example renal denervation;

Treatment of tissue near the urine lumen wall, for example prostate treatment;

Treatment of tissue far from the urine lumen wall, for example prostate cancer.

More detailed examples for treatment and advantages using the present embodiments include phantom pain treatment in which, the target tissue is nerve tissue in the limbs. The catheter cavity may be located in a limb artery. The purpose of the treatment may be reducing phantom pain innervations by denerving the injured nerve.

A point to note is that the attenuation of the ultrasound field is smaller in the fatty tissue around the nerves than in the nerves themselves at the device frequencies. Furthermore the fatty tissue, due to a relatively low heat conduction, isolates the heat created in the nerves. Such phenomena increase the selectiveness of the treatment.

An additional example of treatment is renal denervation.

In this treatment the target is the renal nerves. The catheter cavity is located in the renal artery. The purpose is to reduce pressure on the heart for high blood pressure patients. It is noted that the frequency, power and acoustic beam as per the data and results hereinbelow, treat the nerves without or with minimal damage to the artery. In addition, as in the previous example, the attenuation is smaller in the fatty tissue around the nerves than in the nerves themselves at the device frequencies, which increases the selectiveness of the treatment.

Possible treatment effects in the tissues can be one or more of the following:

Cell necrosis occurring in one or more of: lymphocytes, macrophages, smooth muscle cells, fibroblasts, endothelial cells, and neurons;

Reduced change in the tissue activity including: reducing smooth muscle function, reducing or blocking nerve activity, reducing or blocking the generation of the heart beat potential to the heart muscles;

Mechanical blocking of the vasa-vasorum or\ and the lymph capillary;

Mechanical changes in the collagen fibers, an increase or decrease in stiffness and reducing the maximal tension for tearing;

Biochemical changing in the tissues may include: reducing or preventing plate connection to collagen, and changes of material diffusion through the cell walls.

The device may be operated using typical parameters for acoustic transmission as follows:
Transmission frequency: 8-30 MHz;
imaging frequency 8-60 MHz;
Transmission intensity (SATA): up to 200 w/cm$^2$;
Transmission duration (total time): 1-120 seconds.

The ultrasonic elements transfer the energy to the target tissue, and may also be used as sensors for receiving reflections from the tissue.

The ultrasonic element may also be used as a jet evacuator of fluids for cooling or/and for drug delivery.

The ultrasonic element can be used as a microbubble evacuator.

The ultrasonic element typically includes one or more ultrasonic transceivers including a piezoelectric material or a MEMS element—see FIGS. 2 and 3. Electrodes may provide power to the transceiver. The housing 30 protects the assembly, and an electrical connection may be provided between the electrodes and the catheter wires.

The transceiver element 124 may be, as mentioned, a piezo-electric elements or a MEMS element.

A PIEZO-electric transceiver element may typically be made from PIEZO-electric material, for example: PZT ceramics, PIEZO-electric quartz.

Reference is now made to FIGS. 13A, 13B and 14 which illustrate designs for the ultrasonic element 112. FIG. 13A illustrates a series of shapes where the depth cross-section is rectangular as shown in element 133. The remaining elements in FIG. 13A are viewed from above. Element 135 is rectangular as seen from above. Element 137 is a hexagon. Element 139 is an irregular quadrilateral. Element 140 is a flattened circle. Element 142 is a trapezium. Element 144 is a bullet shape. Element 146 is a trapezium having a shorter dimension between its parallel sides than the trapezium of element 142. Element 148 is a comb shape having a narrow tooth at a first end followed by three wider teeth. Element 150 is a "W" shape, again with a narrow tooth projection at a first end.

FIG. 13B illustrates a closed ring shaped element 152 and an open ring shaped element 154.

FIG. 14 illustrates four variations on a cylindrical element. Element 156 is a filled cylinder. Element 158 is a cylinder with a removable sector. Element 160 is a hollow cylinder having an opening 161 in the lower wall, and element 162 is a hollow cylinder having an open part of the cylinder wall along its length.

In addition the element 112 (as shown in FIG. 8) may be spherical.

In embodiments the transceiver described above does not necessarily include a focal point for the ultrasonic beam. As a result the beam can reach various targets without requiring a precise distance between the element and the target, as will be described in greater detail below.

Possible construction of the transceiver may comprise regular coating methods for piezo elements, and coating materials including one or more of: silver, Ni, gold, copper, or carbon nano-tubes.

Additional coating of the electrodes may improve one or more of the following: the electric conductivity, the acoustic matching, the acoustic reflection or the acoustic amplification.

The additional coating may use any of a variety of materials including polymers, glass and metals.

The PIEZO-electric material may for example comprise: PIEZO-electric ceramics and/or PIEZO-electric quartz. An embodiment as discussed hereinbelow with cooling methods may allow the design to use high hardness ceramics, which have advantages of being of high efficiency, and being small and cheap.

MEMS—the acoustic element can also be implemented using MEMS.

More than one acoustic element can be implemented, for example:
a phased array matrix of elements;
a non-linear geometric array;
a matrix of elements each having different resonant frequencies.

Reference is now made to FIGS. 15A and 15B which illustrate examples for multi-elements transceivers. FIG. 15A is a side view showing five piezoelectric elements 170 mounted on a curved PCB 172. FIG. 15B is a view from above showing two rows of piezoelectric elements 174 and 176.

The housing can made from one or more of the following materials: metals, ceramics, PZT, PIEZO-electric ceramics, glass, polymers or carbons.

The housing may provide an angiogram directional projection for better placing of the element. The housing may further be shaped to provide focusing or to affect fluid flow within the lumen around the element.

The housing may be designed to provide relatively high heat transfer from the element in order to avoid overheating. Typically the heat conductance is a function of shape and of the material used, however standard cooling fins cannot be used in the blood stream as they may cause platelets to break, thus causing blood clots.

The housing can include acoustic damping materials, such as tungsten, or alternatively may be designed to provide an acoustic amplifying effect. As per the discussion above, typically some of the piezoelectric surface is damped and some is provided with acoustic amplification.

A drug delivery capsule may be provided to inject materials into the bloodstream as required by the procedure.

The printed circuit may comprise materials such as hard polymers, flexible polymers, glass-fiber and carbon fiber. Alternatively, the printed circuit may be printed directly on the housing.

As discussed, connection to the acoustic element may use any of wire soldering, paste soldering process, conductive gluing and wire bonding. The connection is preferably both a good heat conductor and a good electrical conductor.

The circuit itself may include vias of copper or other metals for higher heat transfer. One or more printed materials may be provided on the board, including:
copper, metals, polymers, and intermediate materials.

Coatings such as metals, PZT, chemical coatings, isolation coatings, hydrophilic coatings and hydrophobic coatings may be used on different parts of the PCB or housing.

The acoustic transceiver may be connected to the control unit 116 using different kinds of wires including: coax wire, twisted pair, and fiber optic cable.

The acoustic transceiver and the catheter may be coated with different coatings including: an isolation coating, a praline, NiSi, hydrophobic coating, hydrophilic coating, or any kind of biocompatible coating.

As mentioned above, an air pocket may be maintained between the PCB and the piezoelectric element.

The acoustic isolation of the piezoelectric element and consequent increase in efficiency has been mentioned above. This advantage can be used for working in small cavities in order to improve the ability to heat the target volume without at the same time heating the transceiver volume.

Air pockets may be formed by the use of trenches in the PCB structure as illustrated with reference to FIG. 3. or by providing a mounting as shown in FIG. 1 where a gap is defined between the piezoelectric element and the PCB.

Hydrophobic coatings, including praline, may be used to enhance the surface tension effect in order to prevent the water medium from penetrating into the air volume.

The coating may cover the entire air bubble surrounding or part of it and prevent water from penetrating in.

It is noted that the air bubble does not need to be maintained indefinitely. It is sufficient that it is retained for the duration of the ultrasound procedure.

The ultrasonic element may use different anti-resonance values for the working frequency when available. For example one anti-resonance may be used for moderate heating of the tissue, another for power heating of the tissue and yet another for monitoring.

The device may be able to provide an injection jet to the tissue, may provide for increasing fluid flow under the element, say to improve cooling, may evoke micro-bubbles, and may monitor the heating effect and or any injection. The measurement system may include doppler analysis and the heat treatment may use focused or unfocused ultrasound.

In embodiments, the navigation unit 122 may allow the acoustic element to reach the desired location. The navigation unit may further have some auxiliary functions. For example it may deliver the power to the element from the control unit, record measurements from the element and even deliver the measurements to the control unit 116. The navigation unit may further be involved in heat absorption or transfer from the transceiver to the ambient or to the surrounding liquids by providing an additional heat exchange surface extending from the catheter.

The navigation unit may also mechanically hold and place the ultrasonic elements in different locations and at different desired angles, as per FIG. 16. In FIG. 16 a ring configuration 180 may be used, or an angle configuration 182, or a cylindrical configuration 184 or a side configuration 186 or a front configuration 188, each in relation to the catheter.

In embodiments, the navigation unit may include an external navigated control unit. Close to the ultrasonic element, a placing unit may include a balloon, a placing wire or a net or the like.

A heat sink function may including cooling the ultrasonic unit using outside fluid including: blood, urine or CSF. The function may include increasing the heat evacuation by pumping fluid over or from the acoustic unit surface. The function may involve increasing the heat evacuation using internal or external heat conductive material, including: blood passivation coating, or printed coating, or may include increasing the heat evacuation using an internal or external heat conductive balloon.

Heat evacuation may be increased by using an internal or external heat conductive balloon with heat conduction material.

The control unit 116 may provide various kinds of closed loop control and indications on the treatments. The control unit may receive signals from echoes from the tissue. The echo may indicate the area and treatment effect, or the echo can indicate the distance from the cavity wall to the transceiver device. The sensor may be a temperature sensor, which may indirectly sense the temperature of the transceiver by measuring fluid that has just passed the sensor. The temperature may indicate the treatment efficiency, or efficiency of cooling of the cavity, or the cooling or heating of the transceiver.

A power sensor can indicate the output treatment energy. A blood pressure sensor or other like sensors may be provided to indicate reaction to the treatment. A flow sensor can monitor fluid flow in the region of the treatment.

Closed loop effects which do not require the control unit may also be used, as known to the skilled person, for example a coating material on the transceiver surface may be provided that attaches to particles or other materials that come from the treated tissue. The attachment may be used to control the ultrasonic process by making changes to the transceiver frequency during operation.

Materials that can be inserted into the target tissue volume include restenosis prevention materials, for treatment of blood vessels, and materials that are used in drug eluting stents, such as sirolimus, and paclitaxel.

Other materials can be used, say in drug exuding and eluding balloons, and may include materials that are used for bio-degradable stents, anti-Inflammatory materials, medications that may be better presented locally to the tissue than systemically, anti-thrombotic materials, such as Heparin, Aspirin, Ticlopidine, and Clopidogrel, and materials that can cause damage or death to target tissues. Thus materials that can cause nerve death may be supplied for renal denervation.

Also, materials that may help in blocking of the tissue micro-circulation in heating, such as polymers that undergo cross linking, or soluble collagen, or material that may increase the ultrasonic heating of the tissue, such as micro-bubbles that cause higher energy absorption, may be used, or in the latter case generated on site.

Micro-bubble transportation through the cells membrane can be increased using the acoustic treatment, and achieve a multiplicative effect.

Also any kind of medication can be applied.

The transceiver may be positioned on a catheter inside blood-vessels or blood cavities. Ultrasonic irradiation of the target tissue from inside the vessel lumen or cavity outwards may then be provided. Cooling of the piezoelectric element may be achieved by making the design sufficiently conductive and then using blood flow or flow of a fluid from an external source, such as saline that is irrigated into the blood vessel.

The transceiver may be positioned on a catheter inside tissue canals or cavities of body fluids in the body, such as the urethra or urinary bladder, or in the spinal cord or brain ventricles (CNS fluid). Ultrasonic irradiation of the target tissue from inside the canal/cavity outwards may then be provided.

The transceiver may alternatively be positioned on the tip of an endoscope or like device. The endoscope is inserted through a small hole in the skin, and the ultrasonic transceiver is positioned on or near the target tissue.

For cooling, external irrigation is allowed to flow into the area of the treatment cavity. The endoscope tip may for example be positioned inside a balloon like device. The cooling fluid flows inside the balloon. The balloon is positioned next to the treatment tissue location. The ultrasonic transceiver irradiates the target tissue through the balloon wall. Alternatively, the balloon may be positioned on the skin and not inserted through it. The treatment target may be near the skin.

The ultrasonic transceiver may be positioned at a location that allows ultrasonic irradiation of the target tissue. Irrigation of required material in a liquid form may be provided into the blood vessels or lymphatic vessels that supply the perfusion or lymphatic capillaries of the target tissue volume, for example the artery vasa-vasorum.

The method may involve waiting a known time constant for the required material to reach the target tissue.

It is possible to add micro-bubbles to the fluid material in order to help with detection of presence of the material in the target tissue. Micro-bubbles may be detected using ultrasound and sub-harmonic imaging. Micro-bubbles may also improve heating of the target tissue under ultrasonic energy, due to higher absorption of the ultrasonic energy in the tissue volume where they are located.

Applying a thermal effect in the tissue may cause the capillaries to be blocked mechanically or by blood coagulation.

Ultrasound energy applies mechanical force on particles that are present in a liquid, when there is a difference in the acoustic impedance, which is a function of the density multiplied by the speed of sound, between the particles and the liquid. The applied force then pushes particles along the direction of the traveling ultrasonic waves. The mechanical force phenomenon can be used to ensure that required substances arrive at the treatment site.

The ultrasonic transceiver may be positioned in a tissue liquid cavity such as a blood vessel, near the target tissue, while ensuring a liquid spacing between the target tissue and the ultrasonic transceiver irradiating face. As mentioned above a control loop can be used to ensure that the transceiver does not touch the vessel wall and damage epithelium cells.

The required material may be released into the tissue liquid cavity in a way that will cause some of the particles to enter the spacing between the target tissue and the ultrasonic transceiver irradiating face. One way of doing this is to coat the face of the ultrasonic transceiver with the required material, such that the operation of the ultrasonic transceiver may cause particles of the required material to be released into the surrounding liquid.

Another possibility is to add micro-bubbles to the required material fluid in order to detect the material presence in the target tissue. Micro-bubbles may be detected using ultrasound and sub-harmonic imaging.

Yet another possibility is to activate the ultrasonic transceiver so as to apply force on the required material particles to push the particles into the blood vessel wall near the ultrasonic transceiver irradiating face, using the pushing effect mentioned above.

Another possibility is to apply the ultrasonic energy in short high power pulses with long separations between each pulse. This may apply mechanical force, as per the phenomenon discussed above, to the particles to push them into the tissue wall, without heating the tissue wall extensively.

A further possibility is that activation of the captured required material can be achieved by applying additional ultrasonic energy or some other kind of external energy such as a magnetic field on Ferro-electric particles, or an ultrasonic shock-wave to the particles.

The present embodiments may be used for the treatment of renal denervation. The transceiver is simply positioned at 1, 2 or more treatment points, and there is no need for tip manipulation or accurate positioning. The total energizing duration may be between 2 seconds and 2 minutes at each point. Real-time feedback of treatment progress may be provided. The advantages of ultrasonic treatment include directional, localized and remote target tissue effects with minimal damage to other closer tissues, possibly reducing pain, preservation of endothelium and elastic lamina structure and function, so that there is no post treatment stenosis, or at least reduced post treatment stenosis, the avoidance of any mechanical contact on the blood vessel wall, and overall a more robust treatment effect due to real-time feedback.

The following table is a summary of currently contemplated clinical applications.

TABLE 1

Currently Contemplated Clinical Applications

| # | Application Name | Anatomy | Target |
|---|---|---|---|
| 1. | Renal sympathetic nerve modulation | Renal artery | Renal sympathetic nerves |
| 2. | Carotid sympathetic nerve modulation | Carotid artery | Carotid sympathetic nerves |
| 3. | Vagus sympathetic nerve modulation | Aorta | Vagus sympathetic nerve |
| 4. | Peripheral sympathetic nerve modulation | Peripheral blood vessels | Peripheral sympathetic nerves |
| 5. | Pain nerve modulation | Spinal cord cannel | Pain nerves |
| 6. | Restenosis decrease | All relevant arteries | Artery media and adventitia |
| 7. | Vulnerable plaque stabilization | All relevant arteries | Artery media and adventitia |
| 8. | Atherosclerosis pasivation | All relevant arteries | Artery media and adventitia |
| 9. | Plaque volume decrease | All relevant arteries | Artery media and adventitia |
| 10. | Plaque thrombosis decrease | All relevant arteries | Artery media and adventitia |
| 11. | Tetanic limb muscle tonus decrease | Limb arteries or veins | Peripheral motor nerves |
| 12. | Atrial fibrillation prevention | Right atria | Pulmonary vain insertion |
| 13. | Cardiac arrhythmia prevention | Coronary arteries | Cardiac tissue pathology |
| 14. | Liver tumor necrosis | Inferior vena cava | Tumor |
| 15. | None-malignant prostate treatment | Urethra | Sick prostate tissue |
| 16. | Malignant prostate treatment | Urethra | Sick prostate tissue |
| 17. | Artery aneurysms stabilization | All relevant arteries | Aneurysm wall |
| 18. | Aortic aneurysms stabilization | Aorta | Aneurysm wall |
| 19. | Berry aneurysms sealing | Brain arteries | Aneurysm wall |
| 20. | Erectile dysfunction treatment | Internal Iliac | Artery media and adventitia |

Table 2 below summarizes the technology

TABLE 2

Summary of the Technology

Technology
The ultrasonic transceiver:
  1.1.1. Very small: 1.5 × 8 [mm]
  1.1.2. Very thin: 0.8 [mm]
  1.1.3. Very high ultrasonic intensity output: 100 [W/cm$^2$] continuous
  1.1.4. Relatively high work frequencies: 10-25 [MHz].
  1.1.5. Biocompatible coating: Perylene
1.1. The catheter
  1.1.1. Ultrasonic transceiver cooling: vessel blood/liquid flow + catheter braiding as heat sink
  1.1.2. Very flexible treatment tip: 10 mm stiff length. (Pass through 8Fr "hockey-stick" guide catheter)
  1.1.3. Precise and easy torque following TABLE 2-continued Summary of the Technology 1.1.4. Standard 0.014 OTW
1.1.5. Relatively small diameter: 6 Fr
1.2. Distancing fixture
    1.2.1. Distancing transceiver face from artery wall to prevent contact damage, with minimal mechanical forces on artery wall
2. Technology functionality
    2.1. Non-focused ultrasonic beam-like ultrasonic emission
        2.1.1. Simple anatomic
        2.1.2. Big treatment volume cross-section, the size of the transceiver face (differing from focused ultrasound with small treatment volume)
        2.1.3. Relatively even spread of ultrasonic energy in beam cross-section (No need to precise anatomic positioning like in focused ultrasound)
    2.2. Treatment maneuverability and directionality
        2.2.1. Simple maneuvering with nearly 1:1 torquability.
        2.2.2. Simple treatment beam directivity feedback and control from standard angiograph (0, 90, 180, 270)
        2.2.3. No need for high operator skills
        2.2.4. No problem to use contrast agent during treatment
    2.3. Ultrasonic imaging using the unique transceiver - Continuous measurement of distance to artery wall
        2.3.1. Treatment tip real positioning measurement (not possible only from angiography)
        2.3.2. Feedback to prevent high power operation of the transceiver while touching the artery wall.
3. Tissue treatment
    3.1. Very fast treatment:
        3.1.1. Treatment duration of 30-5 sec per treatment point.
        3.1.2. Possibly 4 treatment point per artery for renal denervation
    3.2. Remote and localized effect
        3.2.1. Thermal effect volume in the tissue far from the transceiver face: media, adventitia, Vasa-Vasorum, peri-adventitia, adventitia nerves, peri-adventitia nerves, peri-adventitia capillaries.
        3.2.2. Targeting tissues in varying distances from transceiver face according to treatment parameters (not possible in most focused ultrasonic catheter designs)
        3.2.3. Possibility to apply thermal effect in tissues located 5 mm from the lumen wall. Relevant for peripheral nerves blocking from peripheral arteries.
        3.2.4. Non targeted tissues on the beam path to the target tissue are not damaged.
        3.2.5. Importantly no damage to the endothelium, basal membrane and internal elastic lamina.
    3.3. Tissue selectivity
        3.3.1. Highly selective remote thermal effect in nerve bundles that are covered with thick fat tissue. (most relevant to Renal Denervation in the Renal artery ostium)
        3.4. Treatment special features for Renal Denervation
            3.4.1. Working very close to artery ostium: <10 [mm]
            3.4.2. Working in short arteries: <20 [mm]
            3.4.3. Working in small arteries: 4-3 [mm]
4. Safety
    4.1. The temperature of the blood that flows over the ultrasonic transceiver does not go over 50 C while working in the maximal allowed operation intensity level 50 [W/cm^2].
    4.2. The temperature of the blood that flows over the ultrasonic transceiver does not go over 43 C while working in the therapeutic operation intensity level 30 [W/cm^2]. No need to add external cooling saline injection.
    4.3. The therapeutic treatment on the blood vessel wall is done with no mechanical contact with the vessel wall. No danger of damaging the vessel wall or disrupting any pathologies on the wall (Atherosclerosis plaques)
    4.4. Localized and controlled effect specifically in the targeted treatment volume. No non-controlled energy effects in other tissues (unlike in RF treatment).
    4.5. No blocking of the blood flow during the treatment
5. Possible implications
    5.1. Much less pain in treatment: fast blocking of nerves with no electric excitation of the target nerve and no effect on other nerves (In contrast with Unipolar RF treatment)

Reference is now made to FIGS. 17-22 which illustrate experimental results following use of the device.

FIG. 17 is a histology slide, using H&E stain, and showing the thermal effect in a pig carotid artery. The border of the thermal effect region in the tissue is marked with a dashed line and noted as "Thermal Damage". The setup used was an ultrasonic catheter from inside the blood vessel.

FIG. 18 is a histology slide, using H&E stain, and showing the thermal effect in a pig renal artery. The border of the thermal effect region in the tissue is marked with a dashed line and noted as "Thermal". A necrotic nerve inside the thermal effect region is marked with an arrow and "necrotic nerve" text. The setup involved an ultrasonic catheter from inside the blood vessel.

It is noted that the embodiments cause thermal damage in target tissues far from the lumen internal wall, while causing no thermal damage in the lumen wall internal layer.

Specifically in blood vessels it was shown that thermal damage was achieved in the adventitia or media layers, without causing any apparent damage in the intima layer, either the endothelium or the elastic lamina.

It is believed that the reason for this effect is that the ultrasonic energy heats the artery wall all along the beam, but the blood flow in the lumen cools the tissue that is close to the blood flow, thus the endothelium wall never heats sufficiently to be damaged. It is possible to find a setting for the treatment parameters so to cause heating above 55 C of the tissues far from the blood flow, while the temperature of the intima layer is kept below 55 C.

Exemplary results are shown in FIGS. 19 and 20 which are histology slides wherein analysis and marking of the thermal damage area to a pig Carotid Artery and a Pig Renal Artery respectively, is made by a trained pathologist.

Heating the adventitia or media can cause blocking of the flow inside the small capillaries (called Vasa-Vasorum) in the blood vessel media and adventitia, for example by mechanical crimping due to the shrinking of the connective tissue due to collagen denaturation, or due to thrombotic blocking by a thrombus that is formed in the Vasa-Vasorum because of the thermal damage (the blood flow in these vessels is very low so it can not cool the blood vessel).

FIG. 21 illustrates exemplary results for the above. A histology slide shows analysis and marking of the blocked Vasa-Vasorum with arrows placed by a trained pathologist in a pig Carotid Artery Vasa-Vasorum in the adventitia.

The treatment is intended to provide extensive thermal damage to specific target tissues while keeping nearby tissues undamaged.

It is believed that the ultrasonic energy absorption is different for different kinds of tissue and, and furthermore, the content of collagen fibers may differ.

Specifically it was shown that in nerve fibers that are wrapped by fat tissue, it is possible to cause extensive thermal damage to the nerve tissue, while there is no significant thermal damage in the fat tissue.

FIG. 22 illustrates two histology slides with analysis and marking of the thermal damage, or nerve degeneration area made by a trained pathologist, for a pig renal artery, and nerves in adventitia.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An ultrasonic catheter device sized for insertion within a small vessel for producing ultrasonic beams, comprising:
a transceiver comprising a body vibratable at ultrasonic frequencies and an extensive surface for beam emanation, said transceiver located within an indented window in a circumferential wall of a shaft of said catheter, said transceiver being sunken relative to said shaft wall such that it is seated between raised shaft portions proximally and distally to said transceiver, said transceiver configured to produce an unfocused power beam for thermal tissue damage, the unfocused power beam being produced by vibration over said body of the transceiver and emanating from said extensive surface when said extensive surface is positioned away from a wall of said small vessel at a distance sufficient to allow blood to flow over said extensive surface; and
a controller programmed to vibrate said body to produce said unfocused beam having energy to heat surrounding blood such that blood contacting said extensive surface is heated and its density is reduced, causing it to be displaced by cooler blood which cools said extensive surface by convective cooling to a temperature of 50 degrees Celsius or less.

2. The device of claim 1, wherein said body of said transceiver is mounted on a PCB, wherein trenches are constructed in the PCB for blood flow to enhance said cooling.

3. The device of claim 2, comprising a gas-filled gap between said body and said PCB.

4. The device of claim 3, wherein said gas-filled gap is unsealed and wherein surface tension retains air within said gap when said device is immersed in blood.

5. The device of claim 4, further comprising conductive connections to the PCB across the gas-filled gap, wherein said conductive connections provide thermal linkage between said body and said PCB, thereby enabling the PCB to act as an additional heat dissipation surface for said device.

6. The device of claim 1, further comprising a pump unit for actively pumping said blood around said transceiver.

7. The device of claim 1, wherein said transceiver comprises a piezoelectric element and wherein said vibratable body is a body of said piezoelectric element.

8. The device of claim 1, wherein said transceiver is thermally connected to a heat sink that is located within said circumferential wall of the catheter or in the blood flow; and wherein saline is pumped down the catheter to provide additional fluid flow around the transceiver and/or around the heat sink.

9. The device of claim 1, further comprising a temperature sensor located in association with said transceiver.

10. The device of claim 9, wherein said temperature sensor is located downstream of said transceiver in a flow direction of blood in a vessel within which said device is placed, thereby to measure temperature of blood that has passed said extensive surface.

11. The device of claim 9, wherein said controller is configured for providing said power beam in a duty cycle, said controller being configured to modify said duty cycle and/or applied power in response to changes in temperature indicated by said temperature sensor.

12. The device of claim 11, wherein said controller is configured to modify said duty cycle to control said surface to remain within a range of 40° C. to 50° C.

13. The device of claim 9, controllable to stop said power beam when a temperature sensed by said sensor reaches or exceeds a predetermined safety threshold.

14. The device of claim 1, located at the end of a catheter, and further comprising a temperature sensor located in association with said transceiver, wherein saline is pumped down the catheter to provide additional fluid flow around the transceiver and wherein a rate of pumping is controlled according to changes in temperature sensed by said temperature sensor.

15. The device of claim 14, wherein said controller is configured to modify said rate of pumping to control said surface to remain within a range of 40° C. to 50° C.

16. The device of claim 1, wherein said power beam is provided at a frequency of at least 8 Megahertz, and said vibratable body has a thickness not exceeding 0.3 millimeters, thereby to increase heat transfer from said body.

17. The device of claim 1 further comprising a distancing mechanism for positioning said transceiver at least said distance away from said vessel wall.

18. The device of claim 17, wherein said distancing mechanism comprises a distancing device positioned on said catheter and extending radially away from said transceiver.

19. The device of claim 18, wherein said distancing device is shaped in the form of a spring or a net.

20. The device of claim 1, further comprising one member of the group consisting of: a controllable valve openable into a body lumen for controlling blood flow about said device, a Tec cooler device, metal channels in a PCB, and a distancing device for distancing said transceiver from a vessel wall.

21. The device of claim 20, wherein said body of said transceiver has a thickness below 0.3 millimeters, thereby to increase heat transfer from said vibratable body.

22. The device of claim 1, further comprising one member of the group consisting of: a heat sink thermally coupled to said body for dissipating heat from said device, a thermoelectric cooler device thermally coupled to said body for cooling said body, a printed circuit board wherein the body is mounted on the printed circuit board, and the printed circuit board has channels therein for allowing blood flow to cool said body, a pump for pumping blood around said device to cool said device, and a flow directing structure for directing said flow present in the vessel over the vibratable body in order to cool said device.

23. The device of claim 22, wherein said heatsink comprises braiding along a wall of a catheter to which said device is attached.

24. The device of claim 22, attached to a catheter and wherein said pump is located within said catheter.

25. The device of claim 22, wherein said flow-directing structure comprises a balloon.

26. The device of claim 22, wherein said flow directing structure comprises a shaft and a bending zone on the shaft, the bending zone directing said flow.

27. The device of claim 1, wherein said displacement of heated blood by cooler blood sets up a chimney effect.

28. The device of claim 27, whereby the extensive surface becomes subject to convective cooling when immersed in blood by said chimney effect set up by said unfocused beam.

29. The device of claim 1, wherein said extensive surface is flat.

30. The device of claim 1, wherein said catheter device comprises a flexible distal tip.

31. The device of claim 1, wherein said catheter device comprises more than one ultrasonic transceiver.

32. The device of claim 1, comprising a plurality of transceivers facing different directions, and wherein said controller is programmed to vibrate each of said transceivers to produce said unfocused beam having energy to heat surrounding blood such that blood contacting said extensive surface of each of said transceivers is heated and its density is reduced, causing it to be displaced by cooler blood which cools said extensive surface by convective cooling to a temperature of 50 degrees Celsius or less.

33. An ultrasonic catheter device sized for insertion within a small vessel for producing ultrasonic beams, comprising:
a transceiver comprising a body vibratable at ultrasonic frequencies and an extensive surface for beam emanation, said transceiver located within an indented window in a circumferential wall of said catheter, said transceiver configured to produce an unfocused power beam for thermal tissue damage, the unfocused power beam being produced by vibration over said body of the transceiver and emanating from said extensive surface; said extensive surface positioned such that blood is allowed to flow over said extensive surface;
a controller programmed to vibrate said body to produce said unfocused beam having energy to heat surrounding blood such that blood contacting said extensive surface is heated and its density is reduced, causing it to be displaced by cooler blood which cools said extensive surface by convective cooling to a temperature of 50 degrees Celsius or less;
wherein said body of said transceiver is mounted on a PCB and comprising a gas-filled gap between said body and said PCB; wherein trenches are constructed in the PCB for blood flow to enhance said cooling; wherein said gas-filled gap is unsealed and wherein surface tension retains air within said gap when said device is immersed in blood.

34. An ultrasonic catheter device sized for insertion within a small vessel for producing ultrasonic beams, comprising:
a transceiver comprising a body vibratable at ultrasonic frequencies and an extensive surface for beam emanation, said transceiver located within an indented window in a circumferential wall of said catheter, said transceiver configured to produce an unfocused power beam for thermal tissue damage, the unfocused power beam being produced by vibration over said body of the transceiver and emanating from said extensive surface; said extensive surface positioned such that blood is allowed to flow over said extensive surface;
a controller programmed to vibrate said body to produce said unfocused beam having energy to heat surrounding blood such that blood contacting said extensive surface is heated and its density is reduced, causing it to be displaced by cooler blood which cools said extensive surface by convective cooling to a temperature of 50 degrees Celsius or less;
wherein said body of said transceiver is mounted on a PCB and comprising a gas-filled gap between said body and said PCB; wherein trenches are constructed in the PCB for blood flow to enhance said cooling; wherein said gas-filled gap is unsealed and wherein surface tension retains air within said gap when said device is immersed in blood; and
wherein said device further comprises conductive connections to the PCB across the gas-filled gap, wherein said conductive connections provide thermal linkage between said body and said PCB, thereby enabling the PCB to act as an additional heat dissipation surface for said device.

* * * * *